United States Patent
Puckette et al.

(10) Patent No.: US 11,202,152 B2
(45) Date of Patent: Dec. 14, 2021

(54) ACOUSTIC BEAMFORMING

(71) Applicant: The Regents of the University of California, Oakland, CA (US)

(72) Inventors: Miller Puckette, Encinitas, CA (US); Elliot Patros, San Diego, CA (US); Tahereh Afghah, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/770,764

(22) PCT Filed: Dec. 11, 2018

(86) PCT No.: PCT/US2018/065047
§ 371 (c)(1),
(2) Date: Jun. 8, 2020

(87) PCT Pub. No.: WO2019/118521
PCT Pub. Date: Jun. 20, 2019

(65) Prior Publication Data
US 2021/0176565 A1    Jun. 10, 2021

Related U.S. Application Data

(60) Provisional application No. 62/597,342, filed on Dec. 11, 2017.

(51) Int. Cl.
| | |
|---|---|
| *H04R 3/12* | (2006.01) |
| *H04R 5/04* | (2006.01) |
| *H03G 3/20* | (2006.01) |
| *H04R 1/40* | (2006.01) |
| *H04R 3/00* | (2006.01) |

(52) U.S. Cl.
CPC ............... *H04R 5/04* (2013.01); *H03G 3/20* (2013.01); *H04R 1/403* (2013.01); *H04R 3/005* (2013.01); *H04R 3/12* (2013.01); *H04R 2203/12* (2013.01)

(58) Field of Classification Search
None
See application file for complete search history.

(56) References Cited

U.S. PATENT DOCUMENTS

| 2006/0269072 A1 | 11/2006 | Mao |
| 2009/0154723 A1 | 6/2009 | Choi et al. |

(Continued)

OTHER PUBLICATIONS

Olivieri, F. et al., "Pressure-matching beamforming method for loudspeaker arrays with frequency dependent selection of control points." In Audio Engineering Society Convention 138. Audio Engineering Society, 2015.

*Primary Examiner* — James K Mooney
(74) *Attorney, Agent, or Firm* — Mintz Levin Cohn Ferris Glovsky and Popeo, P.C.

(57) ABSTRACT

A method for acoustic beamforming filter generation may be provided. Applying eigen decomposition to generate a matrix of eigenvectors and a matrix of eigenvalues to solve a pseudoinverse of a matrix of transfer functions. Substituting any eigenvalues in the matrix of eigenvalues that are less than a value of a gain control parameter with the value of the gain control parameter to form a revised matrix of eigenvalues. A matrix of spatial filter coefficients to apply to a sound signal received at least at the first speaker and at the second speaker may be calculated based on the matrix of eigenvectors, the revised matrix of eigenvalues, and a matrix of desired frequency responses.

16 Claims, 21 Drawing Sheets

(56) References Cited

U.S. PATENT DOCUMENTS

| | | |
|---|---|---|
| 2013/0343571 A1 | 12/2013 | Rayala et al. |
| 2014/0064526 A1 | 3/2014 | Otto et al. |
| 2017/0347216 A1 | 11/2017 | Khabbazibasmenj et al. |

…

ACOUSTIC BEAMFORMING

RELATED APPLICATION

This application is a national phase entry of Patent Cooperation Treaty Application No. PCT/US2018/0065047 filed Dec. 11, 2018, entitled "ACOUSTIC BEAMFORMING," which claims priority to U.S. Provisional Application No. 62/597,342 filed Dec. 11, 2017, entitled "ACOUSTIC BEAMFORMING," the disclosure of which are incorporated herein by reference in their entirety.

TECHNICAL FIELD

The subject matter described herein relates generally to acoustic beamforming filter generation.

BACKGROUND

Binaural listening relates to listening with two ears. Acoustic beamforming of speakers or headphones can be used to provide binaural listening by separating audio in right and left channels of an audio signal being produced by the speakers or headphones. Using beamforming, the sound of the left channel can be directed at the left ear of a listener while not being directed at the right ear of the listener. At the same time, the sound of the right channel can be directed at the right ear of the listener while not being directed at the left ear of the listener. The directing of the right channel sounds to the right ear and the directing of the left channel sounds to the left ear can enhance the experience the listener.

SUMMARY

Systems, methods, and articles of manufacture, including computer program products, are provided for acoustic beamforming filter generation. In one aspect, there is provided a system. The system may include at least one data processor and at least one memory. The at least one memory may store instructions that result in operations when executed by the at least one data processor. The operations may include applying eigen decomposition to generate a matrix of eigenvectors and a matrix of eigenvalues to solve a pseudoinverse of a matrix of transfer functions, the transfer functions describing how sound changes from being generated at least at a first speaker and a second speaker and the sound being received at least at a first control point and at a second control point of at least one listener. The operations may also include: substituting any eigenvalues in the matrix of eigenvalues that are less than a value of a gain control parameter with the value of the gain control parameter to form a revised matrix of eigenvalues; and calculating a matrix of spatial filter coefficients to apply to a sound signal received at least at the first speaker and at the second speaker and based on the matrix of eigenvectors, the revised matrix of eigenvalues, and a matrix of desired frequency responses of a sound signal received and transmitted by the first speaker and the second speaker and received at least at the first control point and at the second control point of the at least one listener.

In some variations, one or more features disclosed herein including the following features may optionally be included in any feasible combination. The operations may further comprise calculating, based at least on a first distance and a second distance from at least the first speaker and the second speaker to a location of the first control point and a location of the second control point of the at least one listener, the matrix of transfer functions; and identifying the matrix of desired frequency responses.

The operations may further include receiving location data identifying the location of at least the first control point and the location of the second control point, the location data further identifying locations of the at least a first speaker and a second speaker; and determining, based on the received location data, the first distance and the second distance from at least the first speaker and the second speaker in the array of speakers to at least the first control point and the second control point. The location data may include locations of the first control point and the second control point for a plurality of listeners.

The operations may further include receiving the value of the gain control parameter. The value of the gain control parameter may limit a gain produced by the speaker array to be less than a maximum gain produced by the speaker array for a given frequency.

Calculating the matrix of transfer functions may include calculating, for the first speaker and the second speaker, a first transfer function for a first channel and a second transfer function for a second channel, based at least on the first distance and the second distance from at least the first speaker and the second speaker of the array of speakers to the location of the first control point and the location of the second control point of the at least one listener. The matrix of desired frequency responses may include a value of one for sound of the first channel received at the first control point, a value of zero for sound of the first channel received at the second control point, a value of zero for sound of the second channel received at the first control point, and a value of one for sound of the first channel received at the second control point.

In another aspect, there is provided a method for acoustic beamforming filter generation. The method may include applying eigen decomposition to generate a matrix of eigenvectors and a matrix of eigenvalues to solve a pseudoinverse of a matrix of transfer functions. The transfer functions describe how sound changes from being generated at least at a first speaker and a second speaker and the sound being received at least at a first control point and at a second control point of at least one listener. The method may further include substituting any eigenvalues in the matrix of eigenvalues that are less than a value of a gain control parameter with the value of the gain control parameter to form a revised matrix of eigenvalues; and calculating a matrix of spatial filter coefficients to apply to a sound signal received at least at the first speaker and at the second speaker and based on the matrix of eigenvectors, the revised matrix of eigenvalues, and a matrix of desired frequency responses of a sound signal received and transmitted by the first speaker and the second speaker and received at least at the first control point and at the second control point of the at least one listener.

In another aspect, there is provided a computer program product that includes a non-transitory computer readable storage medium. The non-transitory computer-readable storage medium may include program code that causes operations when executed by at least one data processor. The operations may include applying eigen decomposition to generate a matrix of eigenvectors and a matrix of eigenvalues to solve a pseudoinverse of a matrix of transfer functions. The transfer functions may describe how sound changes from being generated at least at a first speaker and a second speaker and the sound being received at least at a first control point and at a second control point of at least one listener. The operations may further include substituting any eigenvalues in the matrix of eigenvalues that are less than a value of a gain control parameter with the value of the gain control parameter to form a revised matrix of eigenvalues; and calculating a matrix of spatial filter coefficients to apply to a sound signal received at least at the first speaker and at the second speaker and based on the matrix of eigenvectors, the revised matrix of eigenvalues, and a matrix of desired frequency responses of a sound signal received and transmitted by the first speaker and the second speaker and received at least at the first control point and at the second control point of the at least one listener.

In another aspect, there is provided an apparatus for acoustic beamforming filter generation. The apparatus may include means for performing eigen decomposition to generate a matrix of eigenvectors and a matrix of eigenvalues to solve a pseudoinverse of a matrix of transfer functions. The transfer functions describe how sound changes from being generated at least at a first speaker and a second speaker and the sound being received at least at a first control point and at a second control point of at least one listener. The apparatus may further include means for substituting any eigenvalues in the matrix of eigenvalues that are less than a value of a gain control parameter with the value of the gain control parameter to form a revised matrix of eigenvalues; and means for calculating a matrix of spatial filter coefficients to apply to a sound signal received at least at the first speaker and at the second speaker and based on at least the matrix of eigenvectors, the revised matrix of eigenvalues, and a matrix of desired frequency responses of a sound signal received and transmitted by the first speaker and the second speaker and received at least at the first control point and at the second control point of the at least one listener.

Implementations of the current subject matter can include, but are not limited to, systems and methods consistent including one or more features are described as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Binaural systems simulate effects imparted onto sounds by the head, ears, and body of a listener. In some binaural acoustic systems, the listening experience for some listeners can be diminished due to a lack of separation of the right and left channels of audio at the right and left ears of some listeners in a group of listeners. This may be due to crosstalk between the right and left audio channels at one or both of the right and left ears of some of the listeners.

In some example embodiments, beamforming filters are generated. These beamforming filters may be optimized for binaural listening. In some implementations, the amount of right channel audio imparted on the left ears of the listeners and the amount of left channel audio imparted on the right ears of the listeners may be greatly reduced, thereby improving the listening experience of all the listeners.

Although some of the examples refer to binaural systems, the examples may also be implemented in systems handling transaural sound as well.

Figure 1:
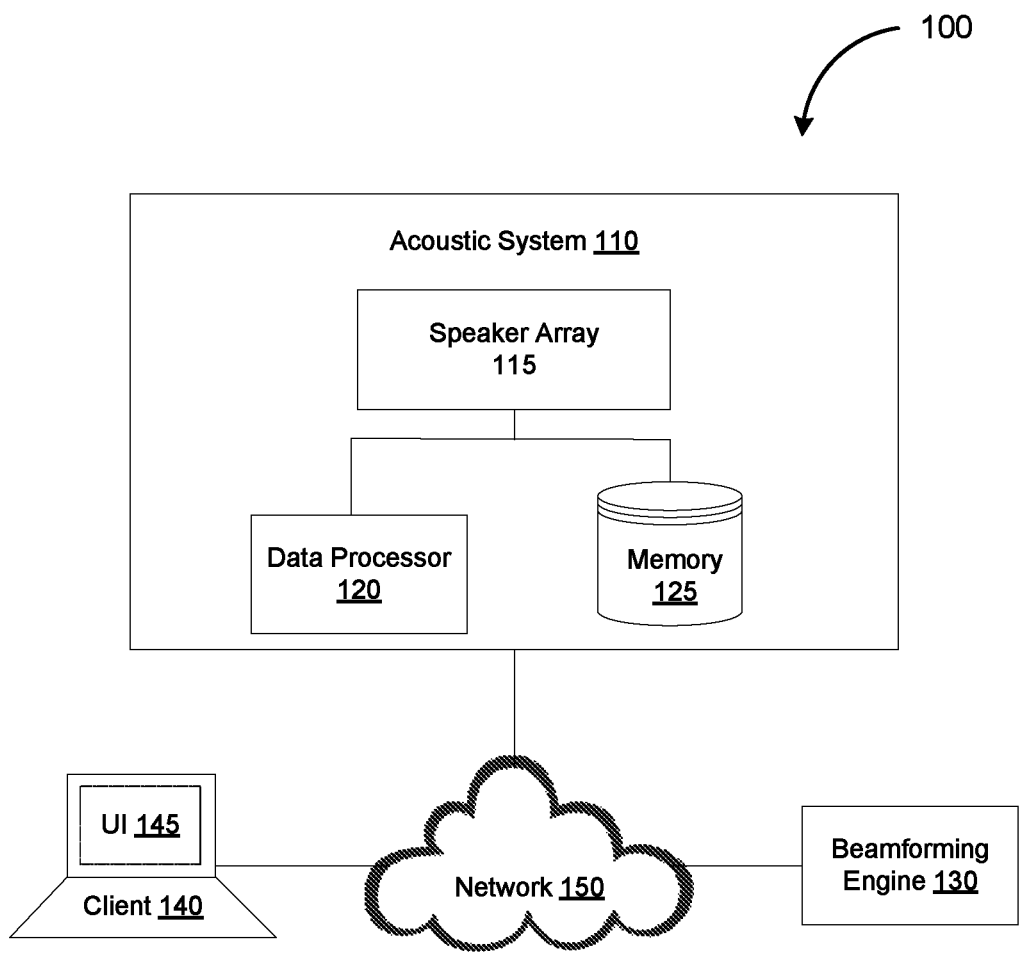
FIG. 1 depicts a system diagram illustrating an acoustic beamforming system.

FIG. 1 depicts a system diagram illustrating an acoustic beamforming system 100, in accordance with some example embodiments. The beamforming acoustic system 100 may include an acoustic system 110, a beamforming engine 130, and a client 140. The acoustic system 110, the beamforming engine 130 and the client 140 may be coupled via a communication link such as a bus or a network 150. The network 150 may be any wired and/or wireless network including, for example, a local area network (LAN), a virtual local area network (VLAN), a wide area network (WAN), a public land mobile network (PLMN), the Internet, and/or the like. Moreover, the acoustic system 110 may include one or more speakers configured as a speaker array 115, a data processor 120, and a memory 125. The memory 125 may be a computer readable medium such as volatile or non-volatile that stores information within the acoustic system 110. The memory 125 may also store data structures representing control point locations, speaker locations, and gain control parameter settings, for example. A control point is a spatial coordinate where a desired transfer function is specified. The filter generation process for the beamforming engine 130 generates filters that mimic the desired transfer function or provide the closest possible approximation of it.

The system 100 may provide beamforming for binaural sound field control. In some implementations, the system 100 may improve performance at dark points, without producing noticeable artifacts at bright points. A "dark point" refers to a location (or control point) relative to a speaker array where sound pressure may be minimized and for which the transfer function may be muted (e.g. the location of the right ear for the left channel). A "bright point" refers to a location (or control point) relative to a speaker array where acoustic interference may be minimized and for which the transfer function may be flattened (e.g., the location of the left ear for the left channel). The system may utilize a regularization strategy (e.g., an eigen decomposition method) for solving the pseudoinverse of ill-conditioned transfer function matrices.

Binaural listening may aim to create an Auditory Virtual Environment (an AVE is the virtual space inhabited by for one or more listeners). AVEs leverage a Head-Related Transfer Function (HRTF), or localization cues, that suggest the direction and distance of a sound's origin relative to a listener. There are multiple playback methods for binaural listening, all of which require controlling the signals arriving at listener's left and right ears, which can be referred to as crosstalk cancellation. In some example embodiments, the system 100 may provide cross talk control for a wider range of frequencies and listening positions, when compared to other methods. In some implementations of system 100, the generated beamforming filters may yield superior imaging of an AVE, when compared to filters generated using PMM, for example.

In some example embodiments, the system 100 may provide for the generation of spatial filters that deliver transaural and/or binaural audio to one or more listeners in arbitrary positions.

To optimally deliver binaural sound to one or more listeners, a high level of control of left and right channel separation (e.g., crosstalk control) may be used. To improve localization accuracy, the system 100 may, in accordance with some example embodiments, prioritize crosstalk control over other acoustic features, such as flattening the frequency response of the system.

As noted, the system 100 may deliver binaural content to multiple listeners. For every listener in a shared acoustic environment, unintentional mixing of left and/or right channels may be prevented by prioritizing directing of notches of the frequency response at dark points, rather than aiming peaks of the frequency response at bright points. Multiple pairs of bright and dark points may be processed simultaneously in multiple listener configurations. The system may implement a single filter for all listeners simultaneously, rather than using separate filter coefficients for each individual listener.

The system 100 may allow for the restrictions to be relaxed with respect to listener positions relative to a beamforming array, which may significantly enlarge the sweet spot (e.g., an ideal position for a listener in a transaural environment). In some implementations, the system 100 may create, for one or more listeners, a very immersive sound in the virtual environment as a consequence of creating a wider sound stage and decreasing sound localization blur.

In acoustic beamforming using a speaker array, a solution for completely segregating the left channel and the right channel may not exist for all frequency and control point combinations (e.g., when the minimum angle between a pair of spatial peaks and notches are wider than the angle between ears). In some implementations, there is provided a way to optimally solve the acoustic beamforming problem of crosstalk between right and left audio channels at both of the right and left ears of each listener in a group of listeners.

Figure 2:
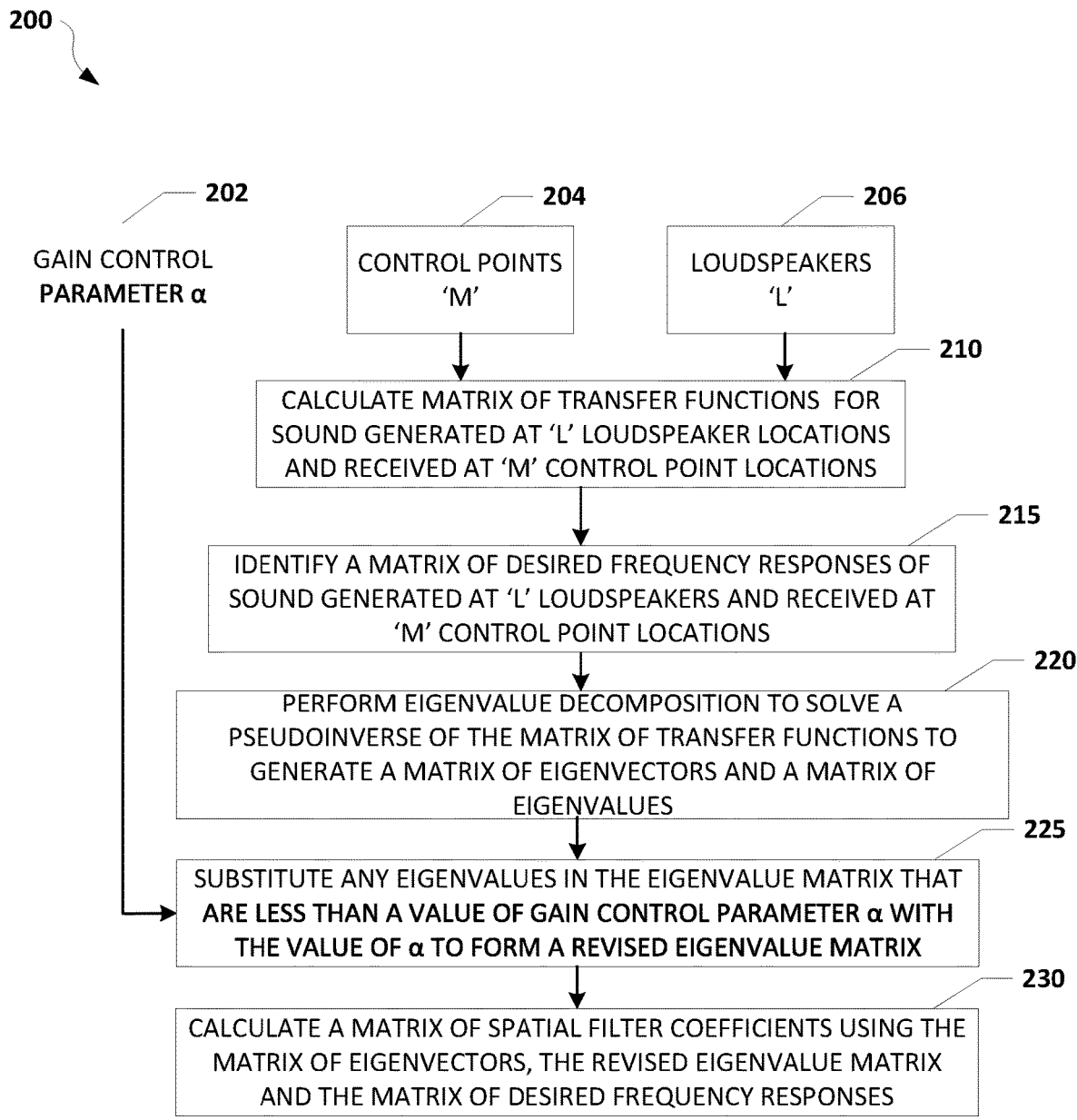
FIG. 2 depicts a flowchart illustrating a process for generating beamforming filters for binaural listening.

FIG. 2 depicts a flowchart 200 illustrating a process for generating beamforming filters for binaural listening. The stages of the flowchart 200 may be executed by a data processor such as the data processor 120 of the acoustic system 110 or by a data processor in the beamforming engine 130 in the acoustic system 100 of FIG. 1.

At stage 210, a data processor calculates a matrix of transfer functions for sound being generated at each of the speakers (e.g., the first speaker and the second speaker), traveling some distance, and being received at the first control point and at the second control point of the at least one listener. In the case of a speaker array of two speakers, the calculation may be based on at least a first distance and a second distance from each of at least the first speaker and the second speaker of an array of speakers to each of a location of a first control point and a location of a second control point of at least one listener, The transfer functions may be calculated using Green's function for acoustics, for example. The transfer functions calculated at stage 210 may be a function of frequency of a sound signal being generated and a function of the distance traveled.

Calculating the matrix of transfer functions at stage 210 may further include calculating, for each of the first speaker and the second speaker, a first transfer function for a first channel and a second transfer function for a second channel. The matrix calculation may be based at least on the first distance and the second distance from each of at least the first speaker and the second speaker of the array of speakers to each of the location of the first control point and the location of the second control point of the at least one listener. The first channel may be a right channel of audio and the second channel may be a left channel of audio.

In some embodiments, the matrix of transfer functions calculated at stage 210 may be calculated based on Green's Function for acoustic propagation, as follows:

$$TF = \frac{e^{-i*2\pi*f*d/c}}{4*\pi*d} \qquad (1)$$

where d is the distance between the source (e.g., the speaker) and the control point, f is frequency and c is the speed of sound.

Location data identifying the location of the first control point and the location of the second control point may be provided at stage 204. The location data provided at stage 204 may be provided by the client 140 or retrieved from the memory 125 of the acoustic system 110 in FIG. 1. The received control point locations may include control points for M listeners. For example, a first control point of a listener may be the location of the right ear of the listener and a second control point of a listener may be the location of the left ear of the listener. Additional location data identifying locations of L speakers including at least a first speaker and a second speaker of a speaker array may be provided at stage 206.

Upon receiving the location data provided at stages 204 and 206, the data processor may determine, based on the received location data, the first distance and the second distance from each of at least the first speaker and the second speaker in the array of speakers to each of the first control point and the second control point. These first and second distances may then be used in calculating the transfer functions at stage 210.

At stage 215, the data processor identifies a matrix of desired frequency responses of sound generated at each of the speakers (e.g., the first speaker and the second speaker) in the speaker array, wherein the sound is received at each of the control points. For example, the matrix of desired frequency responses may be a matrix p including desired frequency responses of sound of the first speaker and the second speaker that are received at the first control point and at the second control point of the at least one listener. In some embodiments, the matrix of desired frequency responses p includes a value of one for sound of a first channel (e.g., a right channel) received at the first control point (e.g., the right ear of a listener), and a value of zero for sound of the first channel received at the second control point (e.g., the left ear of the listener). This matrix of desired frequency responses p further includes a value of zero for sound of the second channel (e.g., the left channel) received at the first control point, and a value of one for sound of the first channel received at the second control point. In this way, the right channel is beamformed toward the right ear of the listener and the left channel is beamformed toward the left ear of the listener. The matrix of desired frequency responses 'p' may be expanded to include desired frequency responses at first and second control points for a plurality of listeners as provided at stage 204.

Proceeding to stage 220, the data processor performs an eigen decomposition to generate a matrix of eigenvectors and a matrix of eigenvalues to solve a pseudoinverse of a matrix of transfer functions. The transfer functions describe how sound changes from being generated at least at a first speaker and a second speaker and being received at least at a first control point and at a second control point of at least one listener. The eigen decomposition and pseudoinverse are further described below.

At stage 225, the data processor substitutes any eigenvalues in the eigenvalue matrix that are less than a value of a gain control parameter 'α' with the value of the gain control parameter 'α' to form a revised eigenvalue matrix. The gain control parameter 'α' may be provided at stage 202 and received at stage 225. The gain control parameter 'α' may be provided at stage 202 by the client 140 or by the beamforming engine 130 of FIG. 1. The value of the gain control parameter 'α' may be chosen to limit a gain produced by the speaker array to be less than a maximum gain produced by the speaker array for a given frequency (e.g., to protect the speakers from overload).

At stage 230, the data processor calculates a matrix of spatial filter coefficients q using eq. (7) below. The matrix of spatial filter coefficients may be calculated using the matrix of eigenvectors extracted at stage 220, the revised eigenvalue matrix extracted at stage 220, and the matrix of desired frequency responses identified at stage 215. The spatial filer coefficients are applied to a sound signal received at each speaker (e.g., the first speaker and the second speaker). The spatial filters cause the sound pressure to closely match the frequency responses specified by the desired frequency response variable p.

In acoustic beamforming applications, the spatial filter coefficients (q) are calculated by solving a linear system of equations $$Zq=p \qquad (2)$$

wherein Z is a M×L matrix of transfer functions between control point (m) and each speaker of the array (l), $q_l$ is filter coefficients for driver l, and $p_m$ is the desired frequency response at a control point m. And, $$q=Z^{-1}p \qquad (3)$$

However, (3) has no solution if Z is not square or if Z is not invertible. Each case is addressed below.

Regarding non-square systems, the matrix Z is square only when the number of control points and speakers are the same, which is not guaranteed in practice. Fortunately, expanding (3) to solve for any arbitrary m and l is trivial using equation (4):

$$q = \begin{cases} (Z^H Z)^{-1} Z^H p, & \text{if } M > L \\ (Z)^{-1} p, & \text{if } M = L \\ Z^H (ZZ^H)^{-1} p, & \text{if } M < L \end{cases} \qquad (4)$$

Eigen Decomposition Pseudoinverse

The system Zq=p of equation (1) may not be well-conditioned. Previous work compensates for this by using Tikhonov regularization. Tikhonov regularization is a conventional way to regularize ill-conditioned matrices. However, Tikhonov regularization causes unintended side effects in the context of transaural beamforming. An alternative regularization method is to invert the eigen decomposition in a way using a gain control parameter α as shown in equation (8) below. An eigen decomposition of Z is represented by:

$$Z=E\lambda E^{-1} \qquad (5a)$$

wherein E is a matrix where columns are eigenvectors of Z, and λ is a matrix with diagonalized elements of eigenvalues of Z. The pseudo-inverse of Z, designated $Z^+$, is calculated as follows:

$$Z^+ = E\lambda^{-1}E^{-1} = E\lambda E^{-1} \quad (5b)$$

The eigen decomposition approach is applied by substituting each case of q from equation (4) as follows:

$$\left.\begin{array}{ll} \text{if } M < L, & Z^H Z \\ \text{if } M = L, & Z \\ \text{if } M < L, & ZZ^H \end{array}\right\} = E\lambda E^{-1} \quad (6)$$

Therefore, by substituting equation (6) into equation (4), the solution for q is:

$$q = \begin{cases} (E\lambda E^{-1})^{-1} Z^H p, & \text{if } M > L \\ (E\lambda E^{-1})^{-1} p, & \text{if } M = L \\ Z^H (E\lambda E^{-1})^{-1} p, & \text{if } M < L \end{cases} \quad (7)$$

wherein $Z^H$ is a Hermitian matrix of the transfer function matrix Z.

Gain Control Parameter

The Gain Control Parameter ($\alpha$) is a variable defined in this algorithm to optimally calculate q for any given speaker array based on the maximum gain that can be produced by the speaker array for a given frequency.

Eigenvalues which are smaller than $\alpha$ are substituted with $\alpha$. Therefore, in the revised eigenvalue or $\lambda$ matrix, $\alpha$ would be the minimum value as is described in equation 8:

$$\lambda_n = \begin{cases} \lambda_n, & \text{if } \lambda_n > \alpha \\ \alpha, & \text{if } \lambda_n < \alpha \end{cases} \quad (8)$$

wherein $1/\alpha$ can be less than the maximum gain a speaker array can produce for a given frequency. PMM methods modify eigenvalues by adding a parameter $\beta$ to all eigenvalues, a technique known as Tikhonov regularization. Modification of eigenvalues as proposed herein, and illustrated in equation 8, is believed to be superior for transaural beamforming.

Figure 3:
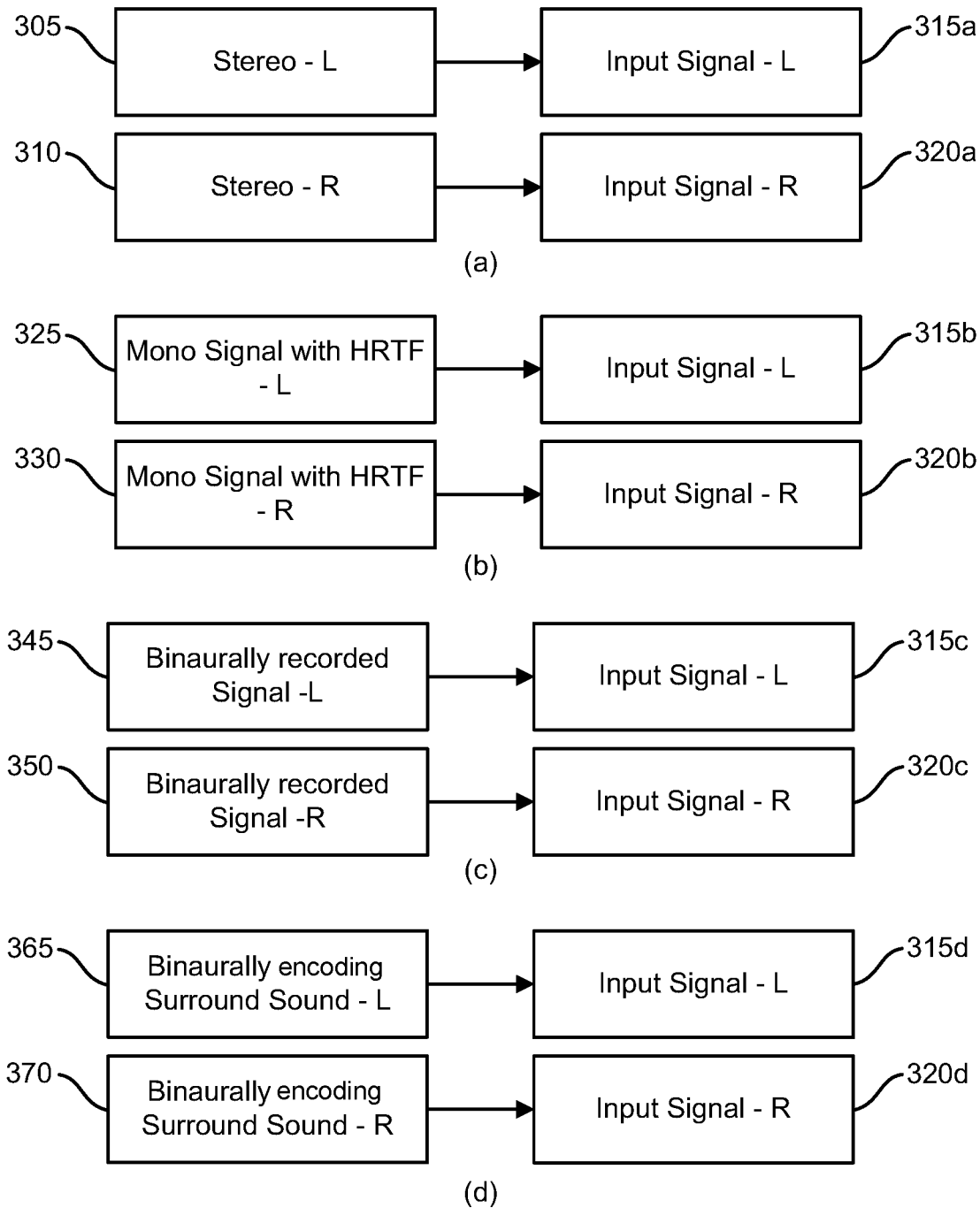
FIG. 3 depicts examples of pre-processing of various audio signals to create an audio signal to be sent to an array of speakers.

FIG. 3 depicts examples of pre-processing of various audio signals to create an audio signal to be sent to an array of speakers. The pre-processing depicted in FIG. 3 is a first part of a process chain illustrating capabilities of the systems and methods disclosed herein in delivering binaural audio from mono, stereo, binaurally recorded sound and surround sound. FIG. 3 depicts pre-processing of various audio signals including left and right channel stereo signals 305 and 310 in FIG. 3a, left and right channel mono signals 325 and 330 in FIG. 3b, left and right channel binaurally recorded signals 345 and 350 in FIG. 3c and left and right channel surround sound signals 365 and 370 in FIG. 3d. Each of the various audio signals 315a to 315d and 320a to 320d in FIGS. 3a-3d can be provided as left and right input signals 315 and 320 as shown in FIG. 4.

In the case of reproducing mono or surround sound using a speaker array, some signal processing methods may be applied before the signal gets processed by the algorithm. Given a 5.1 or 7.1 surround sound for example, a binaural encoding method can be applied beforehand to create left and right channels. Before a mono sound is used as the input signal, it may be convolved with the head-related transfer function (HRTF) corresponding to a desired virtual position.

Figure 4:
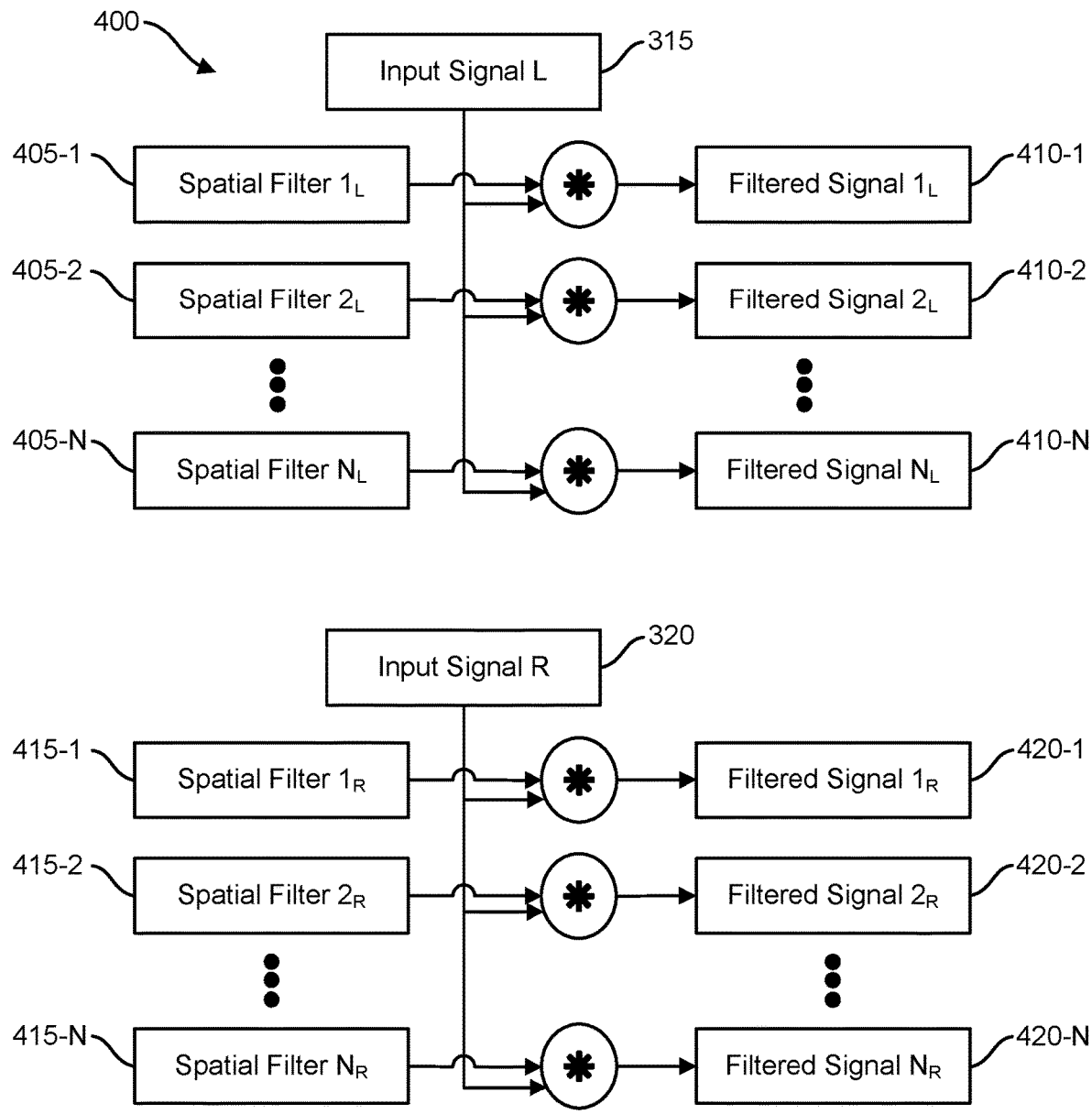
FIG. 4 depicts filtering of the various pre-processed audio signals of right and left channels produced by the processing illustrated in FIG. 3, the filtering being done with beamforming spatial filters generated using the process of FIG. 1.

FIG. 4 depicts filtering of the various pre-processed audio signals of right and left channels produced by the processing illustrated in FIG. 3, the filtering being done with beamforming spatial filters generated using the process of FIG. 2. The filtering of FIG. 4 is a second part of the process chain where generated spatial filters 405-1, 405-2 to 405-N and 415-1, 415-2 to 415-N for left and right channels are one by one convolved with the corresponding left and right input signals 315 and 320 to form filtered left channel signals 410-1, 410-2 to 410-N and filtered right channel signals 420-1, 420-2 to 420-N. Finally, as the last step, the left and right filtered signal made for each driver are added and sent to the corresponding speaker; see FIG. 5.

Figure 5:
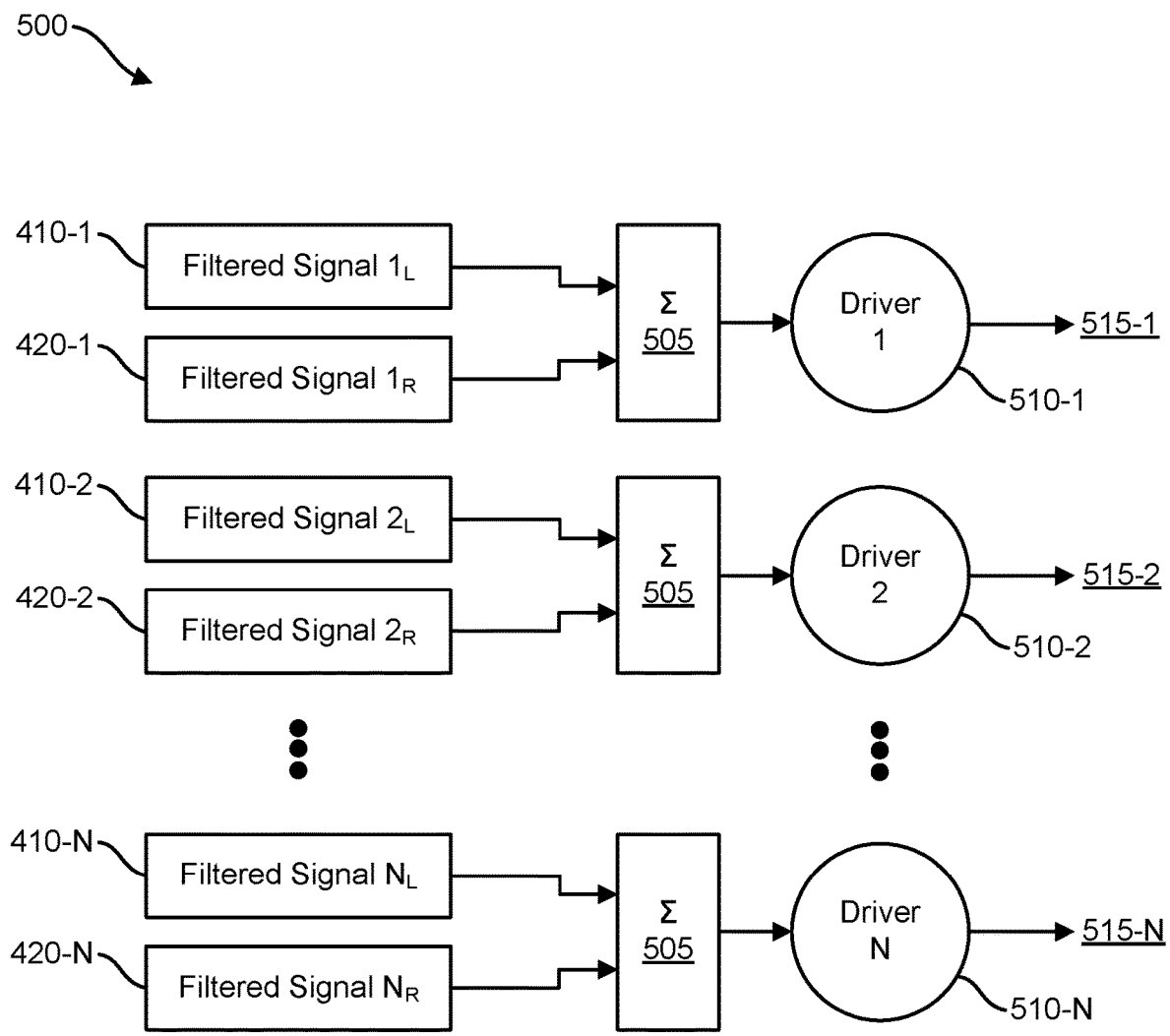
FIG. 5 depicts combining of the filtered right and left channel audio signals produced by the processing illustrated in FIG. 4 and being utilized by "N" drivers to drive the speakers in the speaker array.

FIG. 5 depicts combining of the filtered right and left channel audio signals produced by the processing illustrated in FIG. 4 and being utilized by "N" drivers to drive the speakers in the speaker array. As shown in FIG. 5, filtered left channel signals 410-1, 410-2 to 410-N and filtered right channel signals 420-1, 420-2 to 420-N are combined at summers 505. The summed filtered left and right channel signals are sent to N drivers 510-1, 510-2 to 510-N of the N speakers in the speaker array to produce combined sound signals 515-1, 515-2 to 515-N to be converted to sound by the N speakers.

Figure 6:
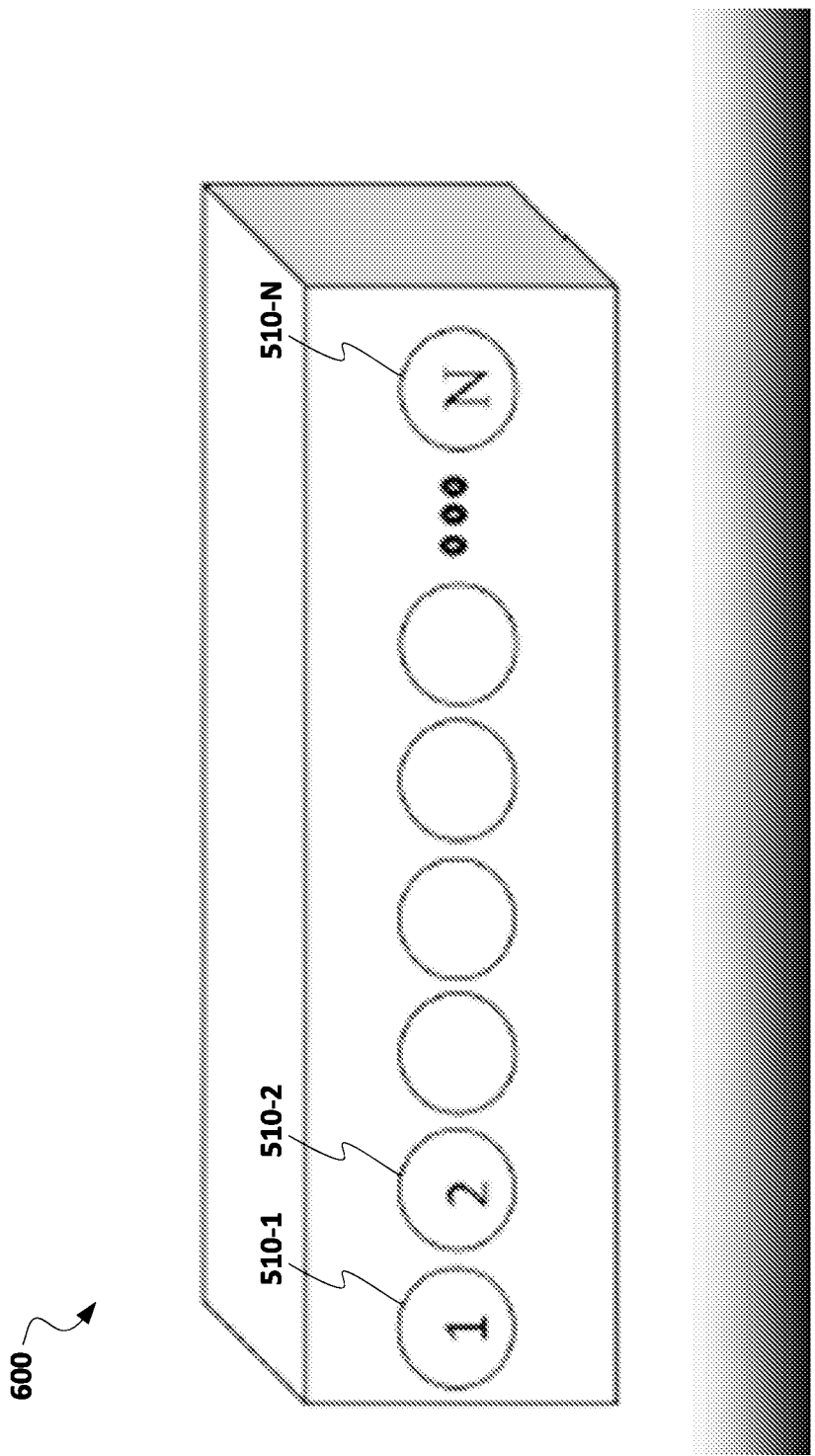
FIG. 6 depicts a speaker array including N drivers being driven by the combined filtered right and left channel audio signals produced by the processing illustrated in FIG. 5.

FIG. 6 depicts a speaker array 600 including N drivers 510-1 to 510-N being driven by the N combined filtered right and left channel audio signals 515-1 to 515-N produced by the N drivers 510-1 to 510-N as shown in FIG. 5.

In some implementations post processing including equalization, normalization, shifting, cropping, and windowing may be implemented.

Equalization—Spatial filters such as those generated at stage 230 of the process 200 in FIG. 2 can be equalized. Linear phase finite impulse response (FIR) filters preserve the phase of the original filters, which maintains the spatial image. This is opposed to, for example, Butterworth filters, which give a maximally flat frequency response at the cost of phase distortion. Using FIR filters may better preserve phase which can be more important for performance of spatial filters than preserving frequency domain magnitude.

Normalization—Digital audio signals can cause clipping in speakers, even if $1 \geq \max|x_n|$; because the peak amplitude of a continuous signal can be higher than that of a discrete signal during transients. This method lets one normalize the spatial filters, q, to a chosen peak value, v, as follows:

$$q = \frac{q * v}{\max q} \quad (9)$$

Shift, crop, and window—Most of the information in q is grouped together in a transient. That also means that for most values of q, the following is true:

$$0 \approx q_n \quad (10)$$

wherein $q_n$ is the nth element of vector q of filters for speaker n in the speaker array.

In some cases it might be desirable to increase the amount of information in the transient of q, while keeping N small. In those cases, q may be calculated with a large N, truncating, q shifting q, cropping q, and windowing q.

The time domain transient in q can be centered by circularly shifting its samples, as follows:

$$q_n = \begin{cases} q_{n+N}, & \text{if } n < N \\ q_{n-N}, & \text{if } n \geq N \end{cases} \quad (11)$$

wherein N is the number of samples in the filter q. Accordingly, the edges of q, which contain nearly no information can be cropped to have a length C, where C is the maximum number of samples in the filter after cropping, for example:

$$q = [q_s, q_{s+1}, \ldots, q_{s+C-1}] \quad (12)$$

wherein s is the index of the filter q after cropping:

$$s = \left\lfloor \frac{N}{2} - \frac{C}{2} \right\rfloor \quad (13)$$

Finally, q can be windowed with a windowing function to prevent discontinuities during filtering, as follows:

$$q = qW^\mu \quad (14)$$

wherein W is a periodic Hanning window, as follows:

$$W_n = 0.5\left[1 - \cos\left(\frac{2\pi n}{N-1}\right)\right] \quad (15)$$

that can be raised to the power μ (see equation 14) which, when 0<μ<1, dampens the edges of q by a lesser degree.

Simulations

In the description below, different scenarios including delivering binaural content to one, two, and three listeners in near and fields are simulated. Several listener's positions are demonstrated in order to illustrate the functionality of the algorithm at different locations.

Figure 7:
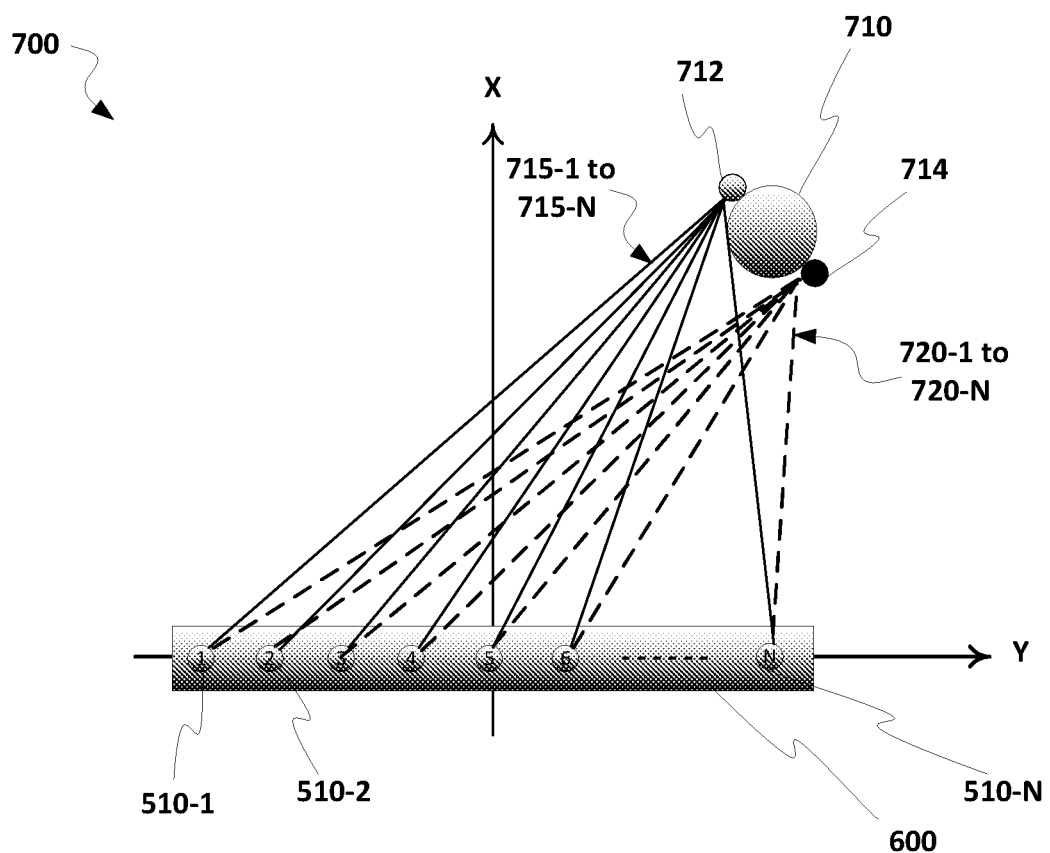
FIG. 7 depicts a speaker array layout and axis system used to illustrate a position of one or more listeners and listener control points (e.g., ears) at various distances from the speaker array.

FIG. 7 depicts a speaker array layout and axis system 700 used to illustrate a position of one or more listeners and listener control points (e.g., ears) at various distances from the speaker array used for each of the simulations. The position of each listener is defined in two dimensions as [$x_i$, $y_i$]. In FIG. 7, positions 715-1 to 715-N indicate a position of a right ear 712 of a listener 710 relative to each of a plurality of speaker drivers 510-1, 510-2 to 510-N included in the speaker array 600 as illustrated in FIG. 6. In addition, positions 720-1 to 720-N indicate a position of a left ear 712 of a listener 710 relative to each of the plurality of speaker drivers 510-1, 510-2 to 510-N included in the speaker array 600 as illustrated in FIG. 6.

FIGS. 8-16 show examples of performance provided by beamforming filters produced by the methods and systems describe above. In those figures, the ears (or control points) of one or more listeners, are shown as circles 810-r for right ears and 810-1 for left ears. And, the 12 drivers 820 (e.g., drivers 510 of FIGS. 5 and 6) of a speaker array (e.g., speaker array 115 of FIG. 1 or speaker array 500 of FIG. 6) are shown as circles at a base of the graphs. The coloration of the graph areas signify a normalized gain of the acoustic pressure located in the graph areas. The normalized gains of the acoustic pressure vary from a low point of 0.0 in the black areas to a high point of 1 in the white areas, with intermediate gains being represented by various grey areas.

Figure 8:
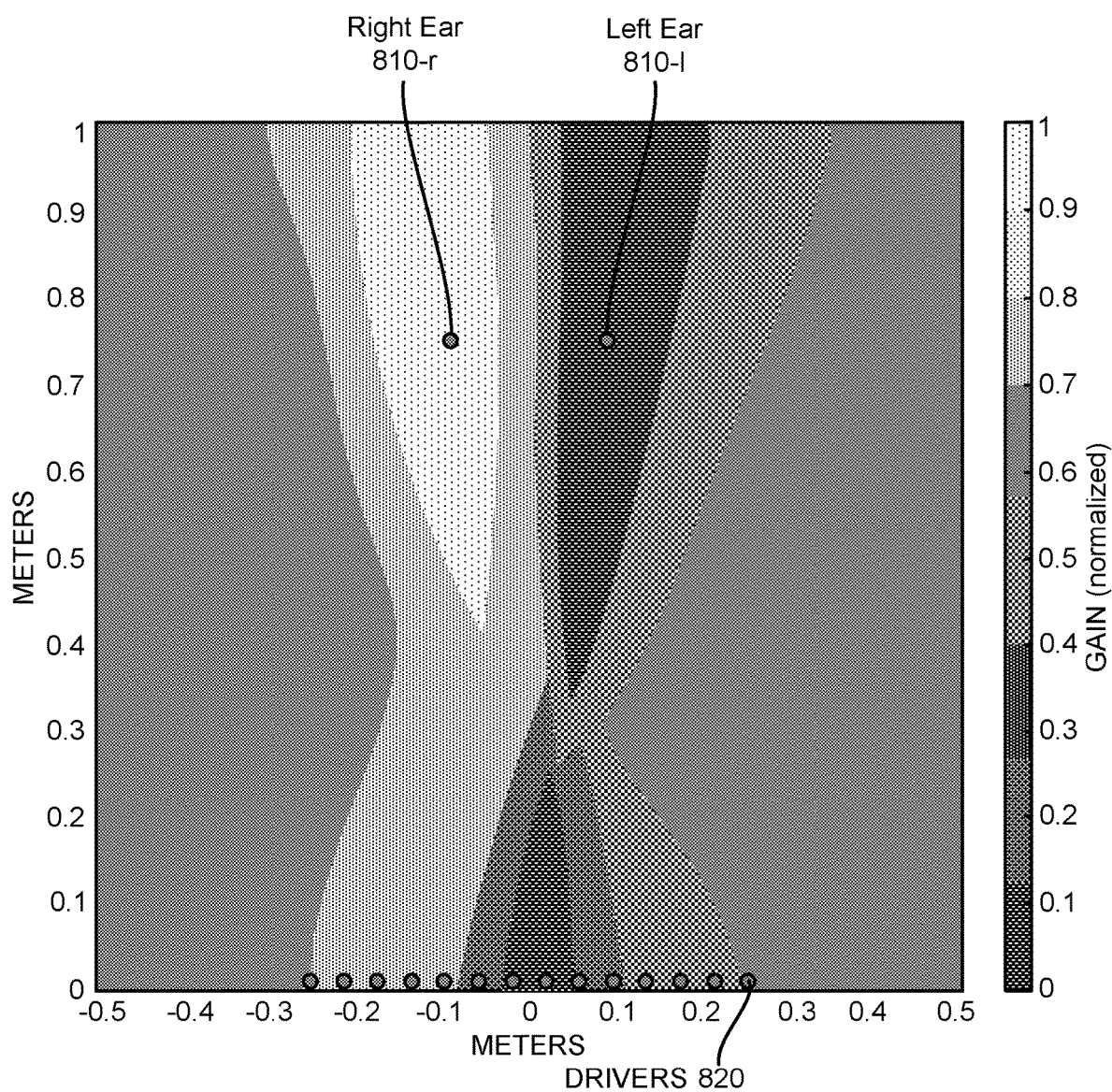
FIGS. 8-16 depict graphs illustrating performance of beamforming spatial filters generated as disclosed herein in relation to dark points and bright points of one or more listeners.
Figure 9:
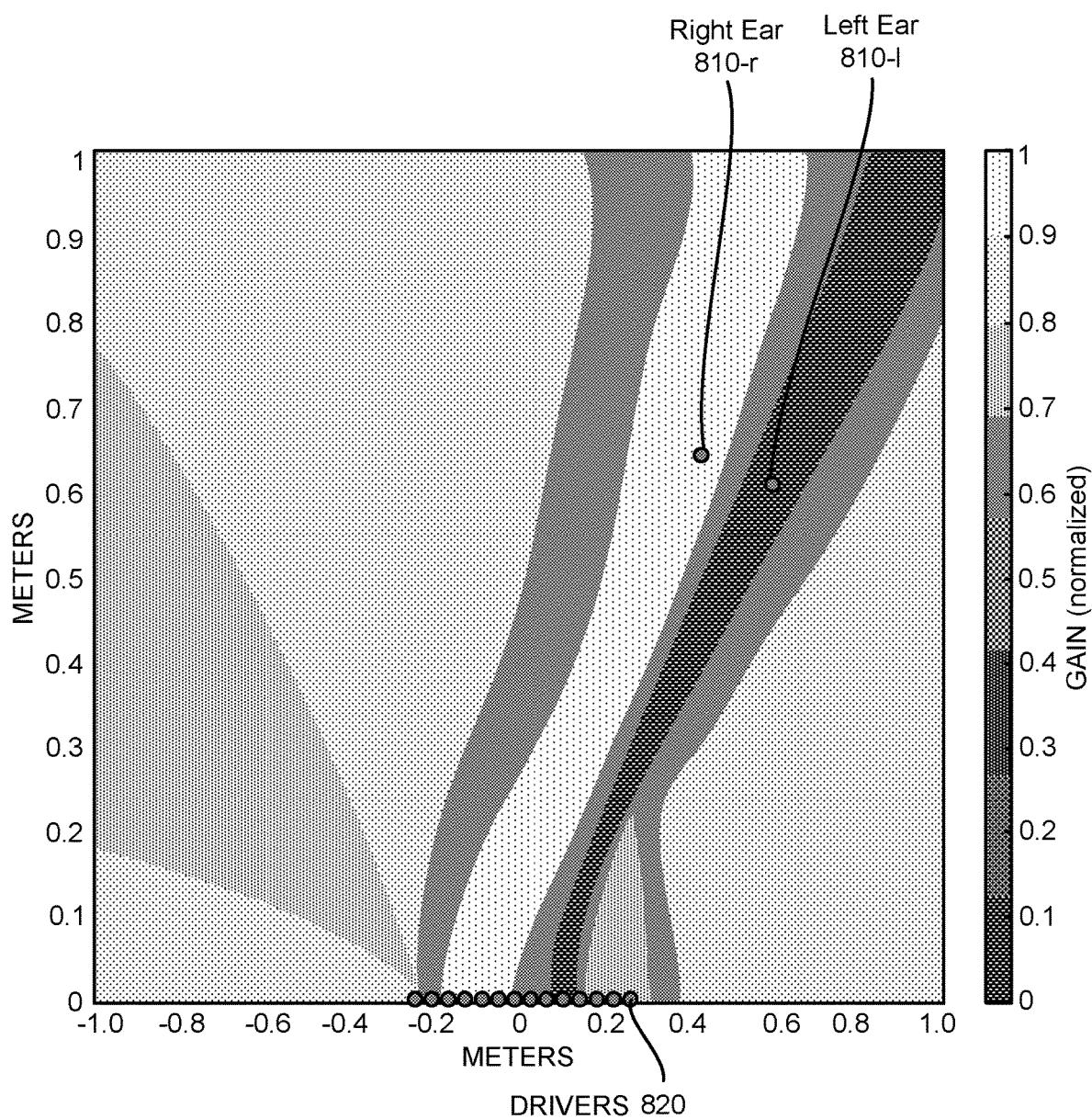
Figure 10:
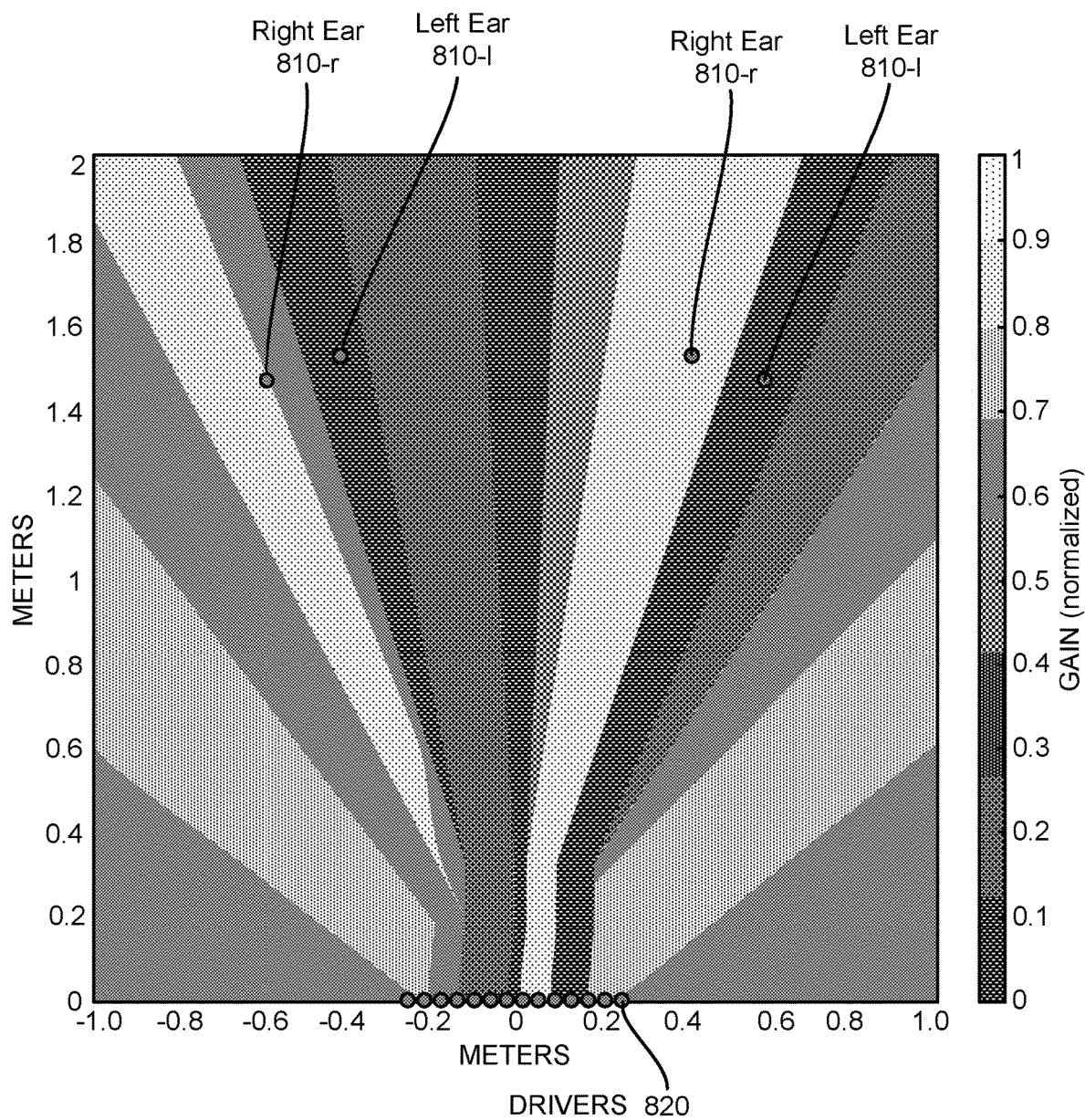
Figure 11:
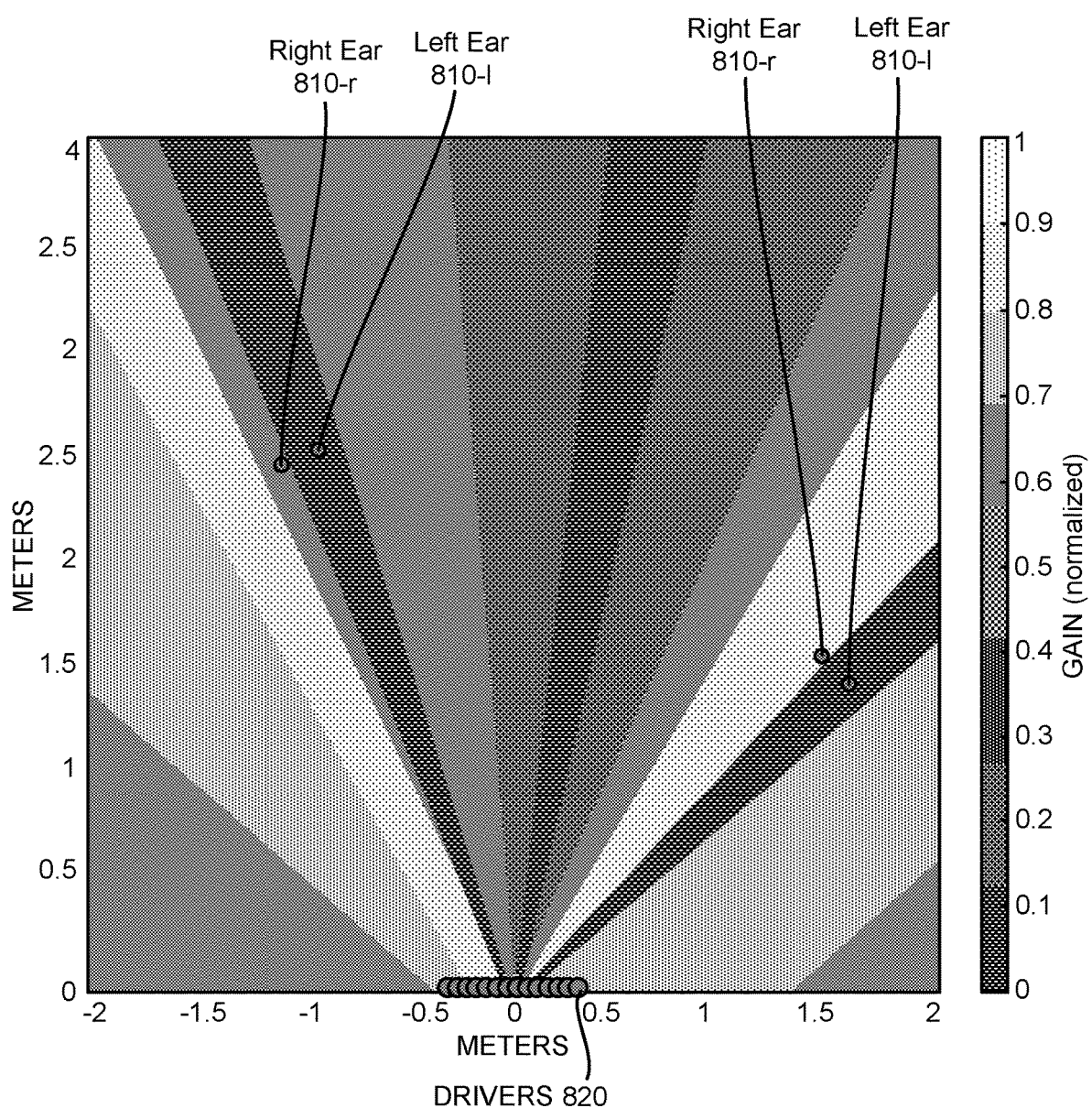
Figure 12:
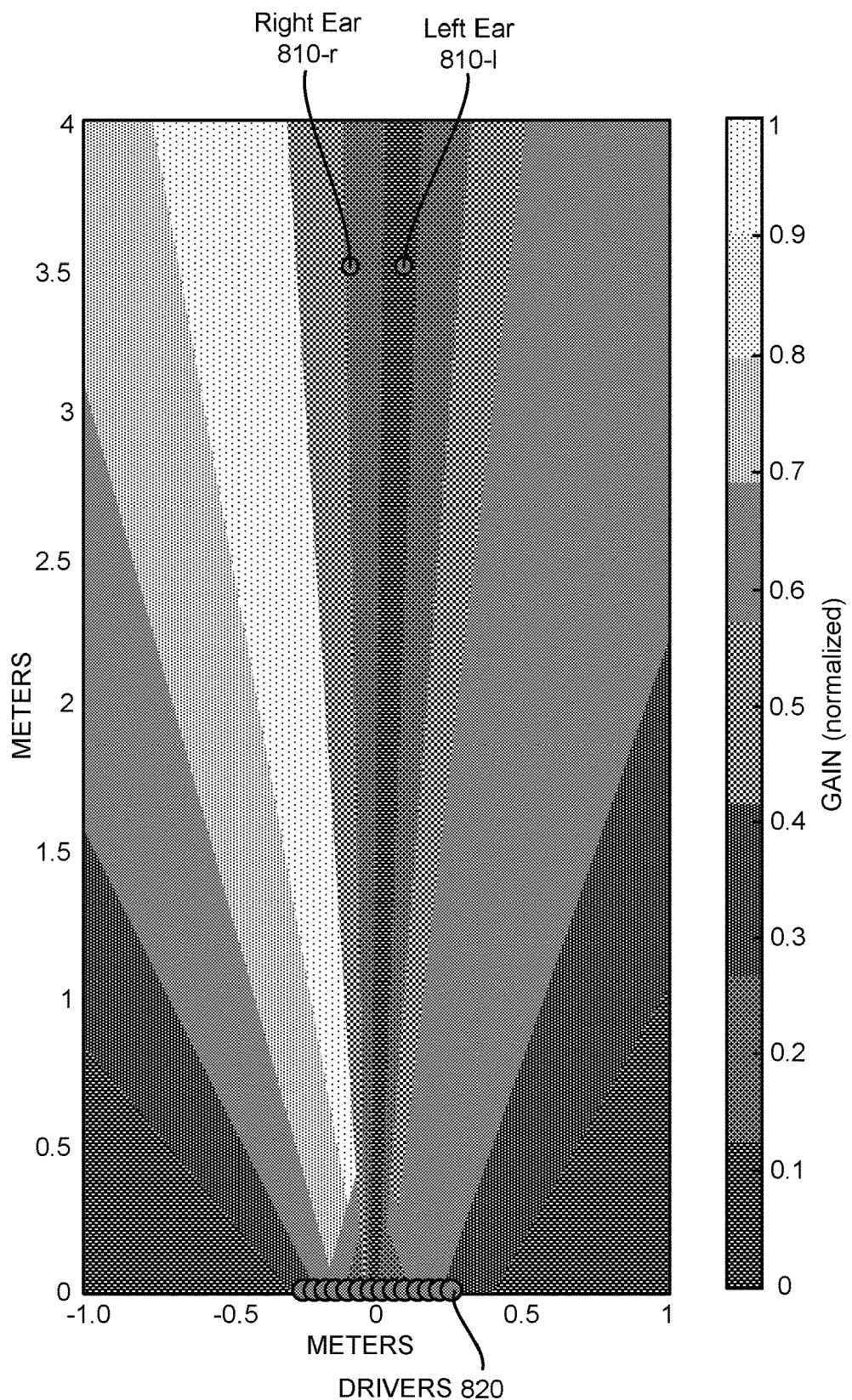
Figure 13:
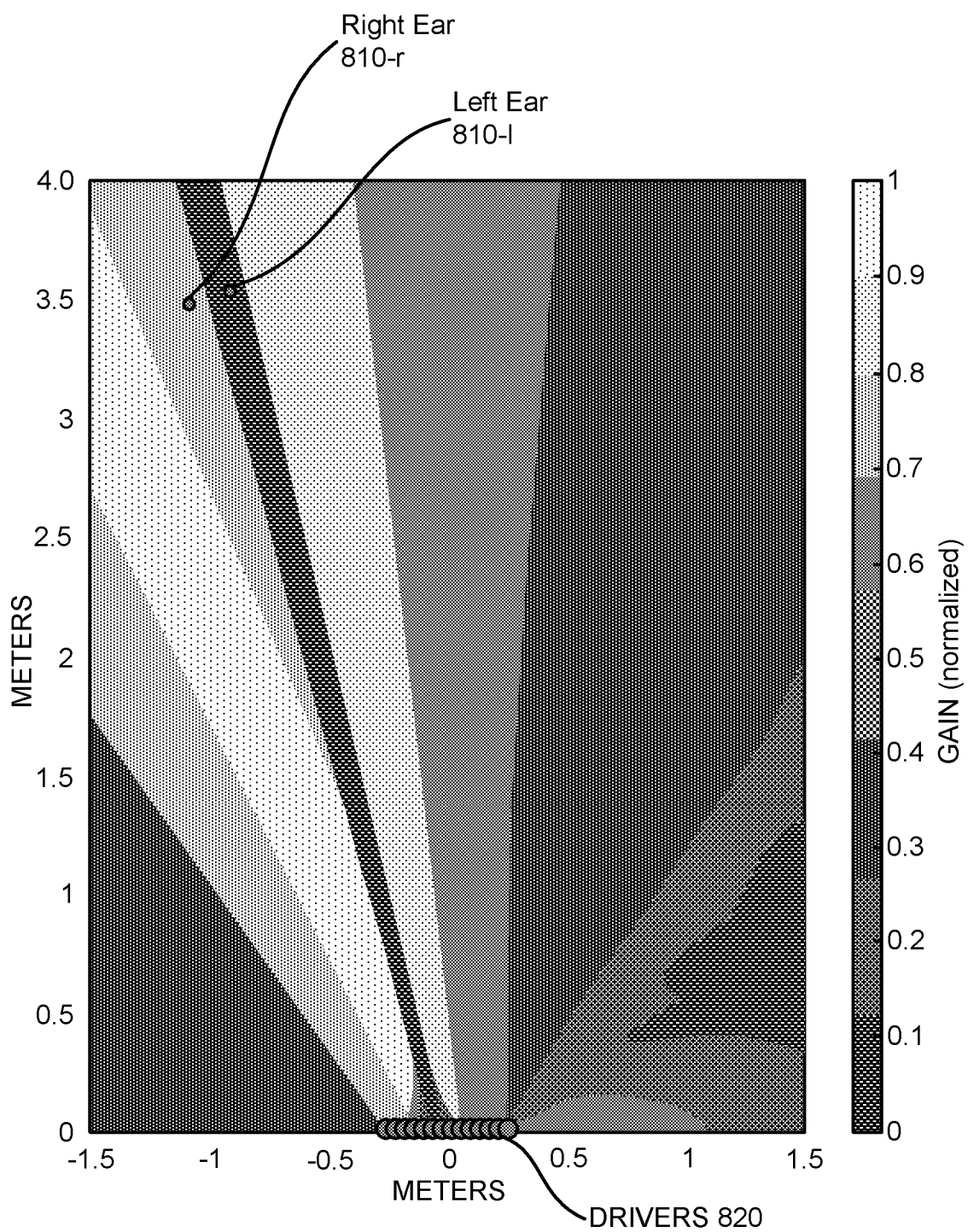
Figure 14:
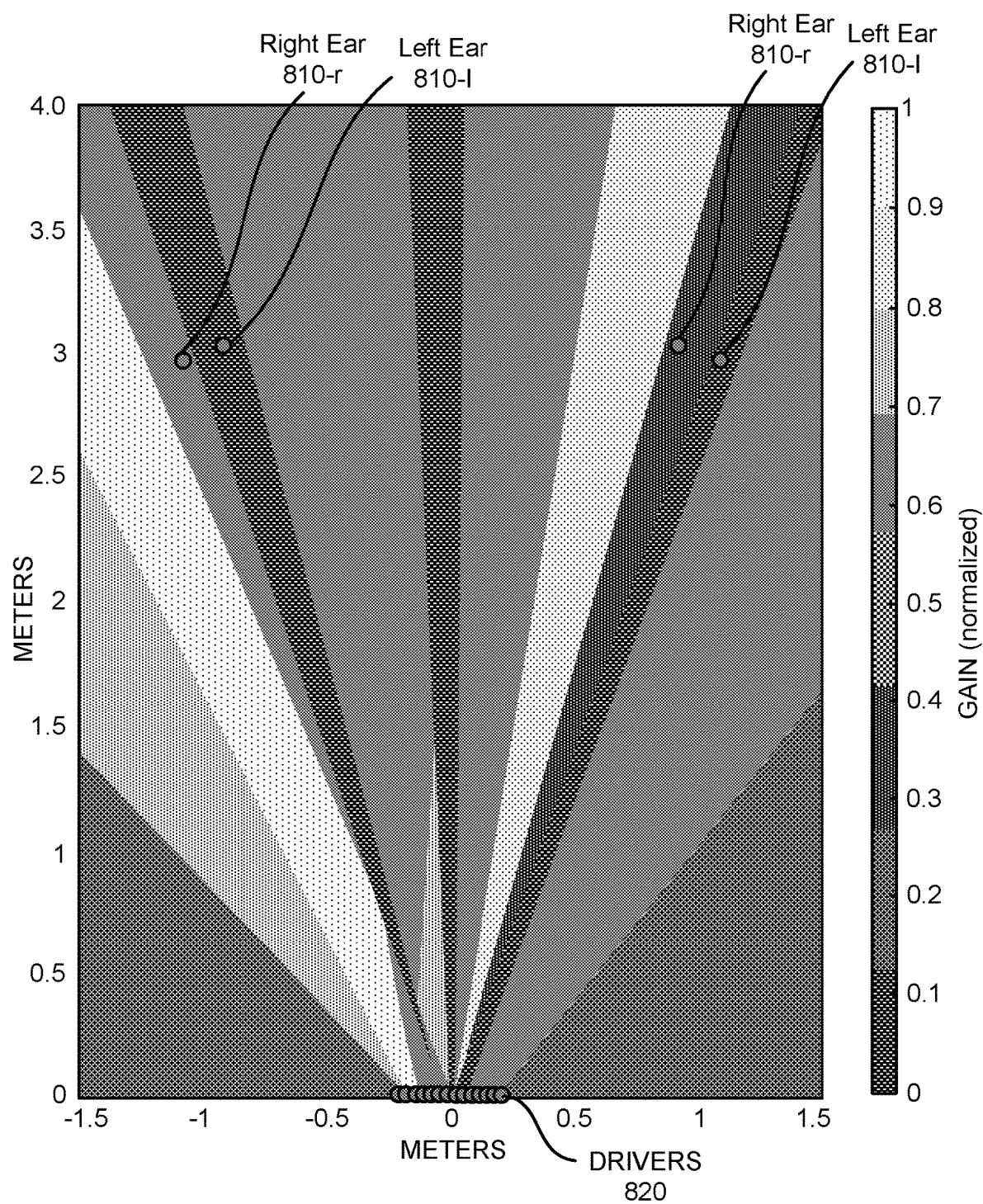
Figure 15:
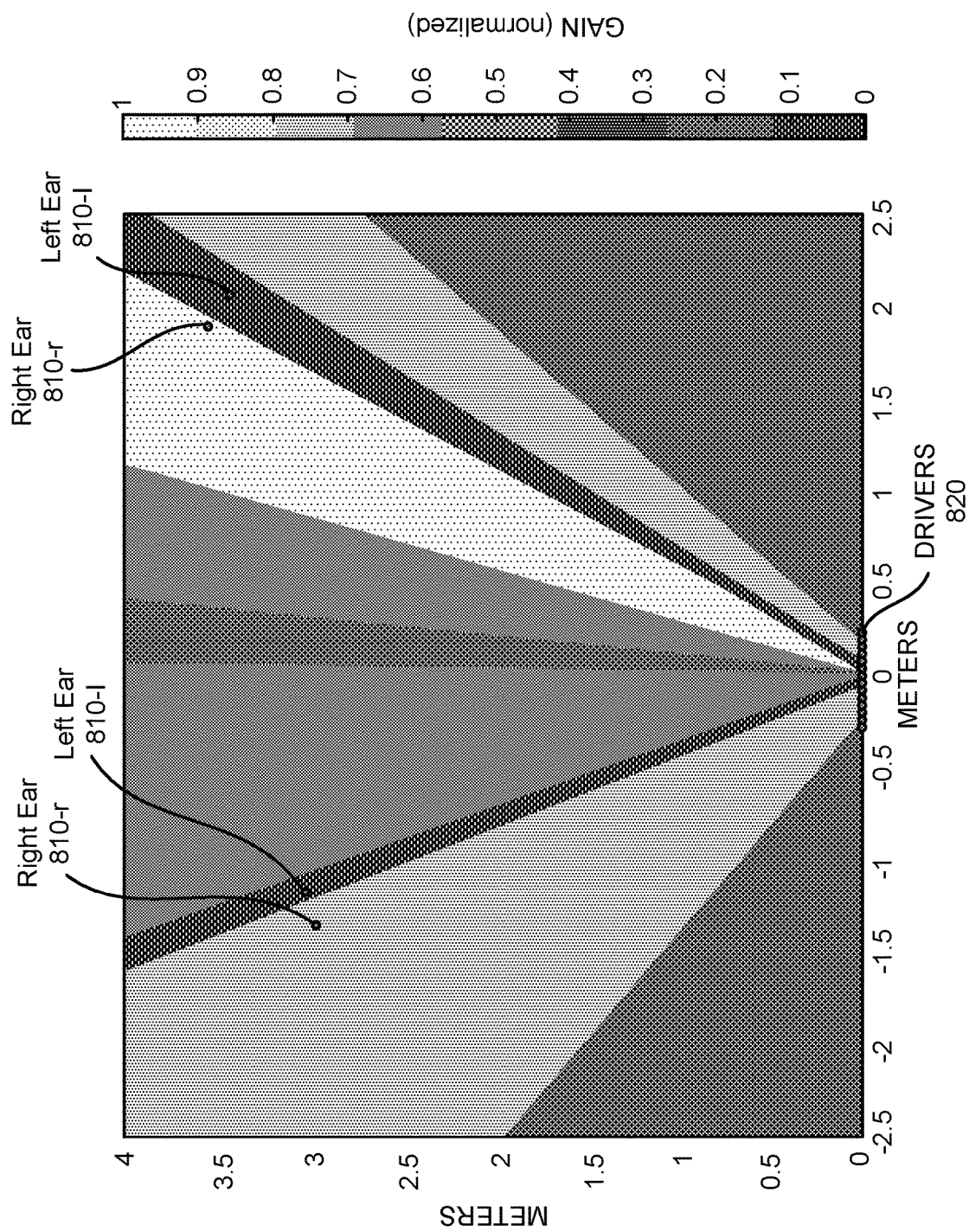
Figure 16:
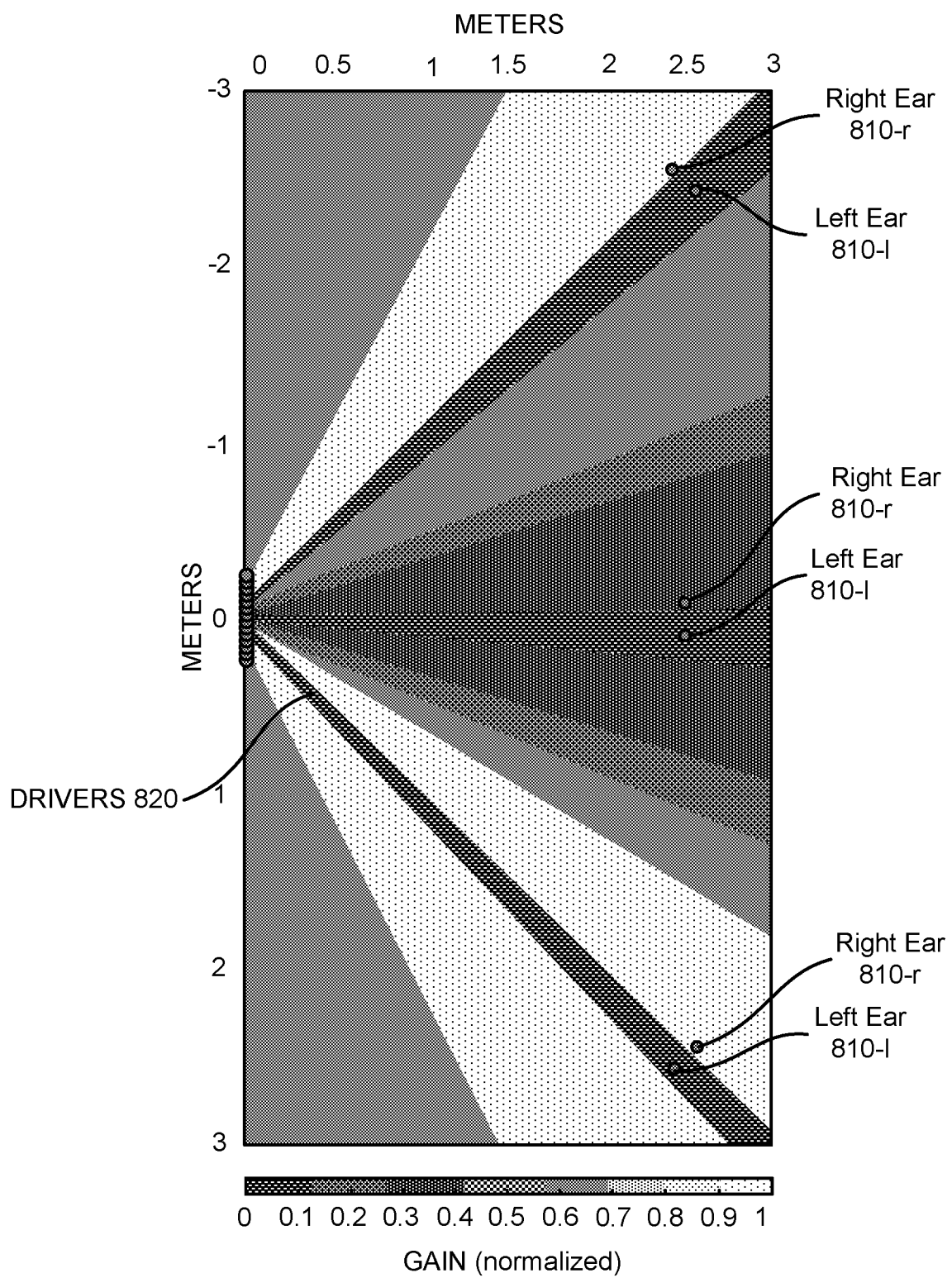

FIGS. 8-16 demonstrate delivering the content of the right channel to the right ear. In other words, the drivers 820 are all right channel drivers, the right ear(s) 810-r are bright point and the left ear(s) 810-1 are dark points. FIG. 8 depicts a single listener on axis at [0.75, 0.0] meters in a near field. FIG. 9 depicts a single listener off axis at [0.75, 0.5] meters in a near field. FIG. 10 depicts 2 listeners in a symmetric pattern off axis at [1.5, −0.5] and [1.5, 0.5] meters in a near field. FIG. 11 depicts 2 listeners in an asymmetric pattern off axis at [2.5, −1.0] and [1.5, 1.5] meters in a near field. FIG. 12 depicts 1 listener on axis at [3.5, 0.0] meters in a far field. FIG. 13 depicts 1 listener off axis at [3.5, −1.0] meters in a far field. FIG. 14 depicts 2 listeners in a symmetric pattern off axis at [3.0, −1.0] and [3.0, 1.0] meters in a far field. FIG. 15 depicts 2 listeners in an asymmetric pattern off axis at [3.0, −1.5] and [3.5, 2.0] meters in a far field. FIG. 16 depicts 3 listeners on and off axis at [2.5, 0.0], [2.5, −2.5] and [2.5, 2.5] meters in a far field.

As can be seen in all of FIGS. 8-16, the right ear control points 810-4 are always located in high gain areas of the graph as represented by the near white coloration, whereas the left ear control points 810-1 are always located in low gain areas of the graph as represented by the near black coloration. Similar performance will be obtained for left ear drivers 820 delivering high gains to the left ears 810-1 while delivering low gains to the right ears 810-4.

Figure 17:
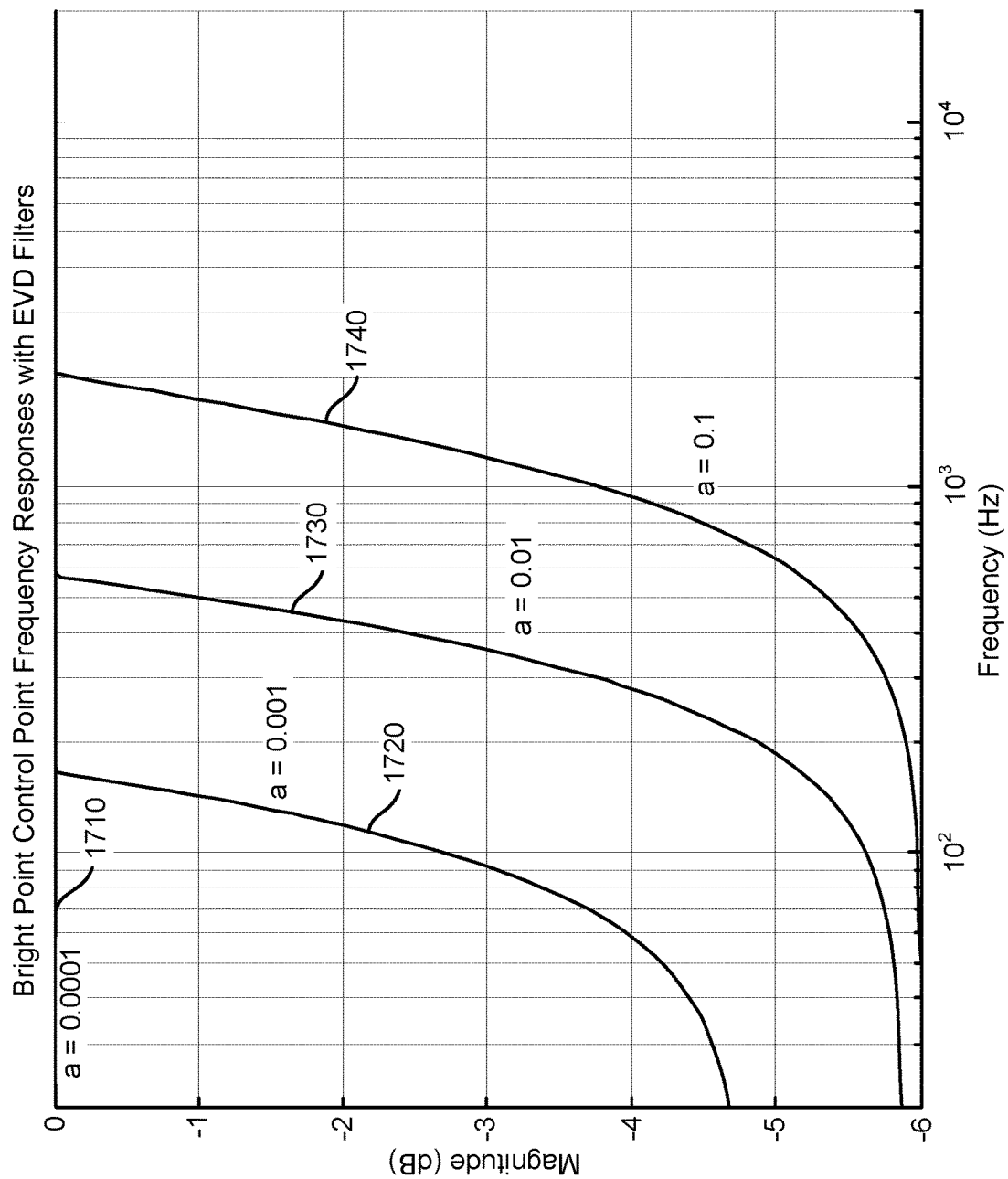
FIG. 17 depicts exemplary frequency responses for various values of $\alpha$ at a bright point control point utilizing beamforming spatial filters generated using eigen decomposition.

FIG. 17 depicts exemplary frequency responses 1710, 1720, 1730, and 1740 for various values of gain control parameter α including α=0.0001, α=0.001, α=0.01 and α=0.1, respectively, at a bright point control point utilizing beamforming spatial filters generated using eigen decomposition methods described herein.

Figure 18:
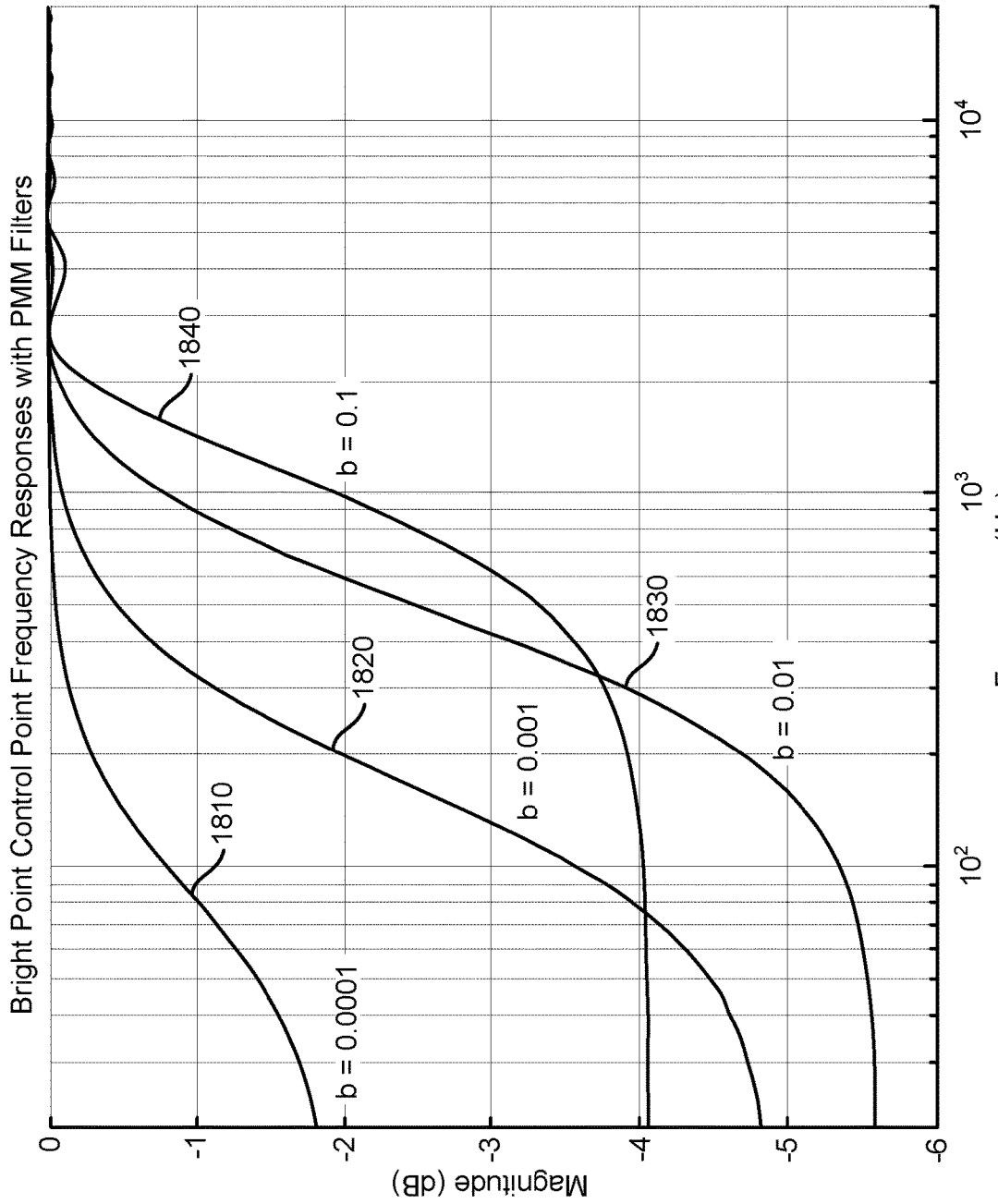
FIG. 18 depicts exemplary frequency responses for various values of $\beta$ at a bright point control point utilizing beamforming spatial filters generated with a pressure-matching beamforming method (PMM) method.
Figure 19:
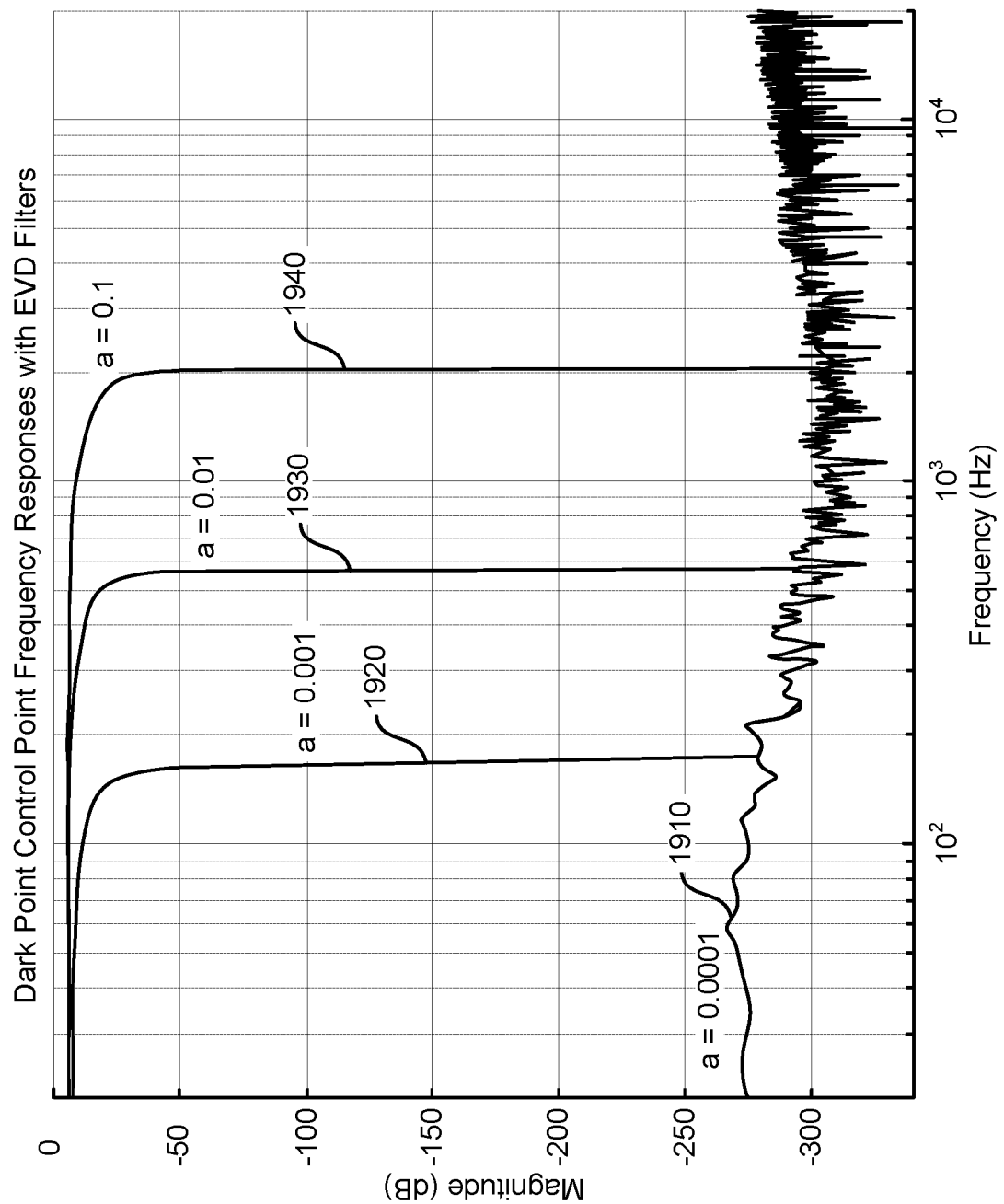
FIG. 19 depicts exemplary frequency responses for various values of a at a dark point control point utilizing beamforming spatial filters generated using eigen decomposition.

FIG. 18 depicts exemplary frequency responses 1810, 1820, 1830, and 1840 for various values of β including β=0.0001, β=0.001, β=0.01 and β=0.1 at a bright point control point utilizing beamforming spatial filters generated with a PMM method;

FIG. 19 depicts exemplary frequency responses 1910, 1920, 1930, and 1940 for various values of gain control parameter α including α=0.0001, α=0.001, α=0.01 and α=0.1, respectively, at a dark point control point utilizing beamforming spatial filters generated using eigen decomposition methods described herein.

Figure 20:
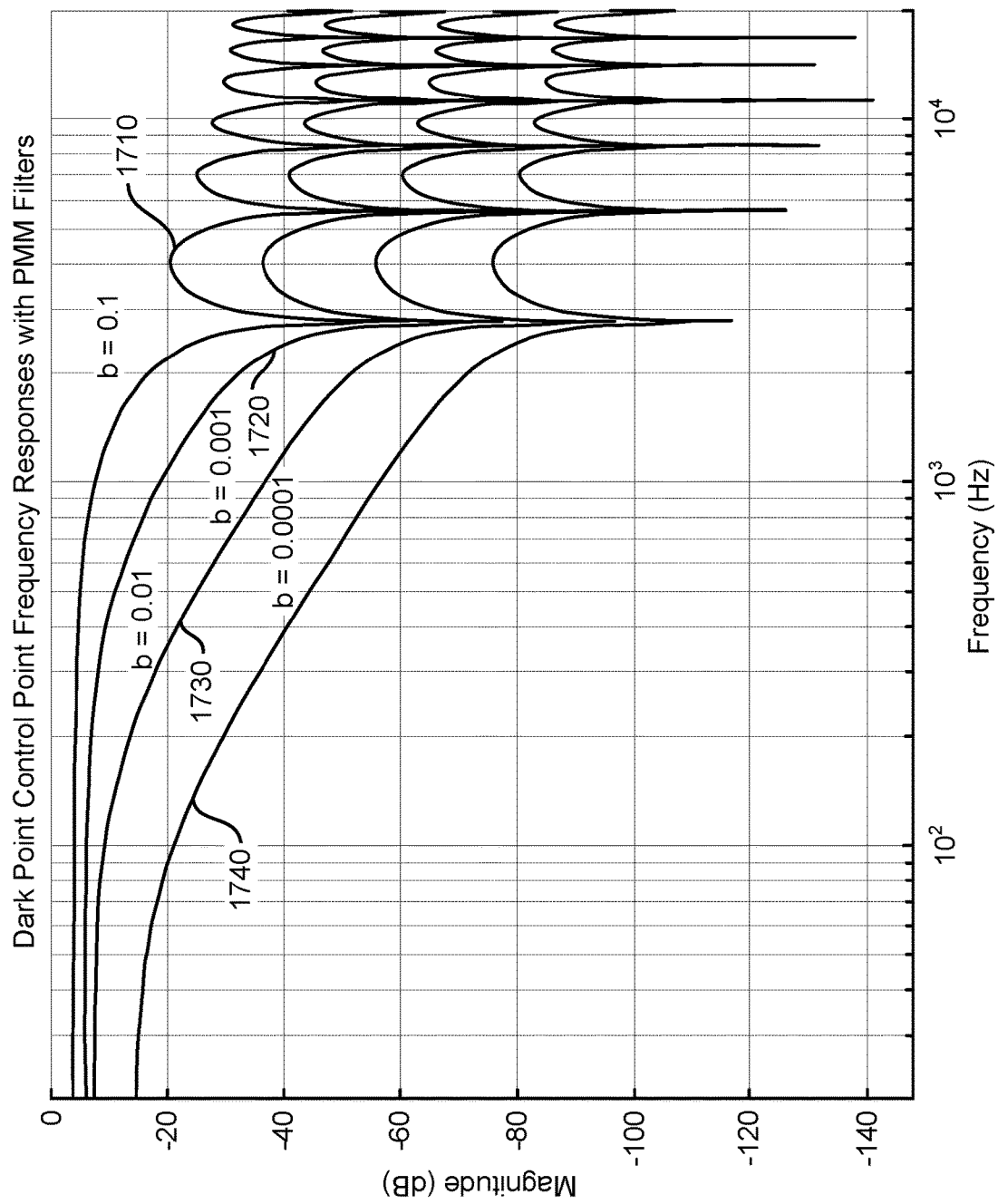
FIG. 20 depicts exemplary frequency responses for various values of $\beta$ at a dark point control point utilizing beamforming spatial filters generated with a PMM method.

FIG. 20 depicts exemplary frequency responses 2010, 2020, 2030, and 2040 for various values of β including β=0.0001, β=0.001, β=0.01 and β=0.1 at a dark point control point utilizing beamforming spatial filters generated with a PMM method.

As can be seen by comparing the frequency responses 1710, 1720, 1730 and 1740 of the eigen decomposition bright point control point with the frequency responses 1810, 1820, 1830 and 1840 of the PMM bright point control point, the magnitudes of the frequency responses for both the eigen decomposition bright point control point and the PMM bright point control point are near unity, 1.0 or 0.0 dB, for most frequencies as prescribed by the desired frequency response matrix 'p' described above.

As can be seen by observing the frequency responses 1910, 1920, 1930 and 1940 of the eigen decomposition dark point control point, the magnitudes of the frequency responses for the eigen decomposition bright point control point are near 0.0, around −250 dB to −350 dB, for most frequencies as prescribed by the desired frequency response matrix 'p' described above. In contrast, the frequency responses 2010, 2020, 2030 and 2040 of the PMM dark point control point are quite a bit higher, around −20 dB to −140 dB for most frequencies.

By comparing the bright point control point and dark point control point frequency responses of the eigen decomposition technique with the bright point control point and dark point control point frequency responses of the PMM method, the performance of the eigen decomposition technique is shown to offer similar or better performance at bright point control points and superior performance at dark points. Thus, the eigen decomposition technique offers an improvement over the PMM method in acoustic beamforming filter generation.

Figure 21:
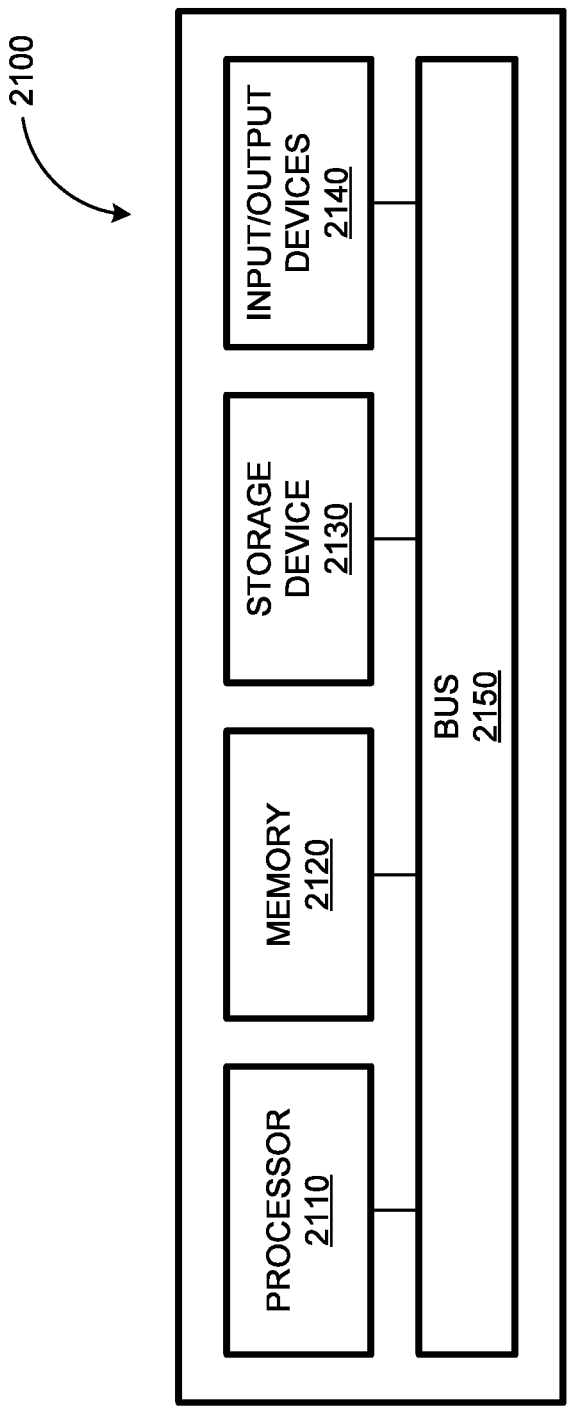
FIG. 21 depicts a block diagram illustrating a computing system, in accordance with some example embodiments.

FIG. 21 depicts a block diagram illustrating a computing system 2100 consistent with implementations of the current subject matter. Referring to FIGS. 1 and 21, the computing system 2100 can be used to implement the beamforming engine 130 and/or any components therein.

As shown in FIG. 21, the computing system 2100 can include a processor 2110, a memory 2120, a storage device 2130, and input/output devices 2140. The processor 2110, the memory 2120, the storage device 2130, and the input/output devices 2140 can be interconnected via a system bus 2150. The processor 2110 is capable of processing instructions for execution within the computing system 2100. Such executed instructions can implement one or more components of, for example, the beamforming engine 130. In some example embodiments, the processor 2110 can be a single-threaded processor. Alternately, the processor 2110 can be a multi-threaded processor. The processor 2110 is capable of processing instructions stored in the memory 2120 and/or on the storage device 2130 to display graphical information for a user interface provided via the input/output device 2140.

The memory 2120 is a computer readable medium such as volatile or non-volatile that stores information within the computing system 2100. The memory 2120 can store data structures representing control point locations, speaker locations, and gain control parameter settings, for example. The storage device 2130 is capable of providing persistent storage for the computing system 2100. The storage device 2130 can be a floppy disk device, a hard disk device, an optical disk device, or a tape device, or other suitable persistent storage means. The input/output device 2140 provides input/output operations for the computing system 2100. In some example embodiments, the input/output device 2140 includes a keyboard and/or pointing device. In various implementations, the input/output device 2140 includes a display unit for displaying graphical user interfaces.

According to some example embodiments, the input/output device 2140 can provide input/output operations for a network device. For example, the input/output device 2140 can include Ethernet ports or other networking ports to communicate with one or more wired and/or wireless networks (e.g., a local area network (LAN), a wide area network (WAN), the Internet).

In some example embodiments, the computing system 2100 can be used to execute various interactive computer software applications that can be used for organization, analysis and/or storage of data in various formats. Alternatively, the computing system 2100 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. Upon activation within the applications, the functionalities can be used to generate the user interface provided via the input/output device 2140. The user interface can be generated and presented to a user by the computing system 2100 (e.g., on a computer screen monitor, etc.).

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively, or additionally, store such machine instructions in a transient manner, such as for example, as would a processor cache or other random access memory associated with one or more physical processor cores.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system for acoustic beamforming filter generation, the system comprising:
   at least one data processor; and
   at least one memory storing instructions which, when executed by the at least one data processor, result in operations comprising:
       performing eigen decomposition to generate a matrix of eigenvectors and a matrix of eigenvalues to solve a pseudoinverse of a matrix of transfer functions, the transfer functions describing how sound changes from being generated at least at a first speaker and a second speaker and the sound being received at least at a first control point and at a second control point of at least one listener;

receiving a value of a gain control parameter, wherein the value of the gain control parameter limits a gain produced by a speaker array to be less than a maximum gain produced by the speaker array for a given frequency;

substituting any eigenvalues in the matrix of eigenvalues that are less than the value of the gain control parameter with the value of the gain control parameter to form a revised matrix of eigenvalues; and calculating a matrix of spatial filter coefficients to apply to a sound signal received at least at the first speaker and at the second speaker and based on at least the matrix of eigenvectors, the revised matrix of eigenvalues, and a matrix of desired frequency responses of the sound signal received and transmitted by the first speaker and the second speaker and received at least at the first control point and at the second control point of the at least one listener.

2. The system of claim 1, wherein the operations further comprise:

calculating, based at least on a first distance and a second distance from at least the first speaker and the second speaker to a location of the first control point and a location of the second control point of the at least one listener, the matrix of transfer functions; and identifying the matrix of desired frequency responses.

3. The system of claim 2, wherein the operations further comprise:

receiving location data identifying the location of at least the first control point and the location of the second control point, the location data further identifying locations of the at least a first speaker and a second speaker; and determining, based on the received location data, the first distance and the second distance from at least the first speaker and the second speaker in the array of speakers to at least the first control point and the second control point.

4. The system of claim 3, wherein the location data comprises locations of the first control point and the second control point for a plurality of listeners.

5. The system of claim 2, wherein calculating the matrix of transfer functions comprises calculating, for the first speaker and the second speaker, a first transfer function for a first channel and a second transfer function for a second channel, based at least on the first distance and the second distance from at least the first speaker and the second speaker of the array of speakers to the location of the first control point and the location of the second control point of the at least one listener.

6. The system of claim 1, wherein the matrix of desired frequency responses comprises a value of one for sound of the first channel received at the first control point, a value of zero for sound of the first channel received at the second control point, a value of zero for sound of the second channel received at the first control point, and a value of one for sound of the first channel received at the second control point.

7. A method for acoustic beamforming filter generation, the method comprising performing eigen decomposition to generate a matrix of eigenvectors and a matrix of eigenvalues to solve a pseudoinverse of a matrix of transfer functions, the transfer functions describing how sound changes from being generated at least at a first speaker and a second speaker and the sound being received at least at a first control point and at a second control point of at least one listener;

receiving a value of a gain control parameter, wherein the value of the gain control parameter limits a gain produced by a speaker array to be less than a maximum gain produced by the speaker array for a given frequency;

substituting any eigenvalues in the matrix of eigenvalues that are less than the value of the gain control parameter with the value of the gain control parameter to form a revised matrix of eigenvalues; and calculating a matrix of spatial filter coefficients to apply to a sound signal received at least at the first speaker and at the second speaker and based on at least the matrix of eigenvectors, the revised matrix of eigenvalues, and a matrix of desired frequency responses of the sound signal received and transmitted by the first speaker and the second speaker and received at least at the first control point and at the second control point of the at least one listener.

8. The method of claim 7, further comprising:

calculating, based at least on a first distance and a second distance from at least the first speaker and the second speaker to a location of the first control point and a location of the second control point of the at least one listener, the matrix of transfer functions; and identifying the matrix of desired frequency responses.

9. The method of claim 8, further comprising:

receiving location data identifying the location of at least the first control point and the location of the second control point, the location data further identifying locations of the at least a first speaker and a second speaker; and determining, based on the received location data, the first distance and the second distance from at least the first speaker and the second speaker in the array of speakers to at least the first control point and the second control point.

10. The method of claim 9, wherein the location data comprises locations of the first control point and the second control point for a plurality of listeners.

11. A computer program product comprising:

a non-transitory computer readable storage medium storing program code that causes operations when executed by at least one data processor, the operations comprising:

applying eigen decomposition to generate a matrix of eigenvectors and a matrix of eigenvalues to solve a pseudoinverse of a matrix of transfer functions, the transfer functions describing how sound changes from being generated at least at a first speaker and a second speaker and the sound being received at least at a first control point and at a second control point of at least one listener;

receiving a value of a gain control parameter, wherein the value of the gain control parameter limits a gain produced by a speaker array to be less than a maximum gain produced by the speaker array for a given frequency;

substituting any eigenvalues in the matrix of eigenvalues that are less than the value of the gain control parameter with the value of the gain control parameter to form a revised matrix of eigenvalues; and calculating a matrix of spatial filter coefficients to apply to a sound signal received at least at the first speaker and at the second speaker and based on at least the matrix of eigenvectors, the revised matrix of eigenvalues, and a matrix of desired frequency responses of the sound signal received and transmitted by the first speaker and the second speaker and received at least at the first control point and at the second control point of the at least one listener.

12. The computer program product of claim 11, wherein the operations further comprise calculating, based at least on a first distance and a second distance from at least the first speaker and the second speaker to a location of the first control point and a location of the second control point of the at least one listener, the matrix of transfer functions; and identifying the matrix of desired frequency responses.

13. The computer program product of claim 12, wherein the operations further comprise:

receiving location data identifying the location of at least the first control point and the location of the second control point, the location data further identifying locations of the at least a first speaker and a second speaker; and determining, based on the received location data, the first distance and the second distance from at least the first speaker and the second speaker in the array of speakers to at least the first control point and the second control point.

14. The computer program product of claim 13, wherein the location data comprises locations of the first control point and the second control point for a plurality of listeners.

15. The computer program product of claim 12, wherein calculating the matrix of transfer functions comprises calculating, for the first speaker and the second speaker, a first transfer function for a first channel and a second transfer function for a second channel, based at least on the first distance and the second distance from at least the first speaker and the second speaker of the array of speakers to the location of the first control point and the location of the second control point of the at least one listener.

16. The computer program product of claim 15, wherein the matrix of desired frequency responses comprises a value of one for sound of the first channel received at the first control point, a value of zero for sound of the first channel received at the second control point, a value of zero for sound of the second channel received at the first control point, and a value of one for sound of the first channel received at the second control point.

* * * * *